United States Patent [19]
Fujii

[11] Patent Number: 4,594,895

[45] Date of Patent: Jun. 17, 1986

[54] ULTRASONIC MEASUREMENT METHOD, AND APPARATUS THEREFOR

[75] Inventor: Tadashi Fujii, Fujinomiya, Japan

[73] Assignee: Terumo Kabushiki Kaisha, Tokyo, Japan

[21] Appl. No.: 651,963

[22] Filed: Sep. 18, 1984

[30] Foreign Application Priority Data

Oct. 6, 1983 [JP] Japan .................. 58-186027

[51] Int. Cl.[4] ........................... G01N 29/04
[52] U.S. Cl. ...................... 73/599; 128/660
[58] Field of Search ........... 73/599, 628, 615, 625; 128/660

[56] References Cited

U.S. PATENT DOCUMENTS

| | | | |
|---|---|---|---|
| 3,681,977 | 8/1972 | Wendt et al. | 73/615 |
| 3,713,329 | 1/1973 | Munger | 128/660 |
| 4,202,215 | 5/1980 | Meyer | 73/599 |

FOREIGN PATENT DOCUMENTS

EP0066343 8/1982 European Pat. Off. .

OTHER PUBLICATIONS

IEEE Transactions on Biomedical Engineering, vol. BME-27, No. 2, Feb. 1980, pp. 76-83, New York (US). M. Kadaba et al.: "Attenuation and Backscattering of Ultrasound in Freshly Excised Animal Tissues", *p. 76, right-hand col., line 8; p. 80, right-hand col., line 40.

*Primary Examiner*—Anthony V. Ciarlante
*Attorney, Agent, or Firm*—Frishauf, Holtz, Goodman & Woodward

[57] ABSTRACT

A method and apparatus wherein two probes are arranged to oppose each other on either side of an object under investigation and each of two probes emits ultrasonic waves to measure the acoustic characteristics of the object respectively.

Mean attenuation coefficients for small intervals can be calculated solely from the received echo signals by processing signals indicative of echos of the ultrasonic waves from the two probes. Reflection coefficients can be calculated from the mean attenuation coefficients obtained. In addition, a distribution image of either of the mean attenuation coefficient and reflection coefficient distributions are obtained from these mean attenuation coefficients and reflection coefficients for the small intervals.

10 Claims, 32 Drawing Figures

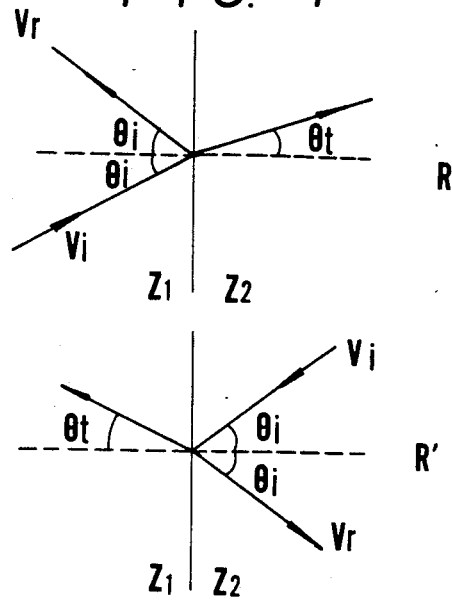
FIG. 4
FIG. 5
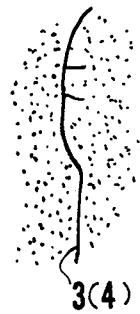
FIG. 6
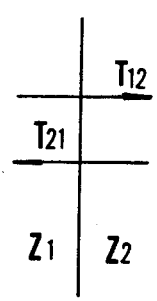

ULTRASONIC MEASUREMENT METHOD, AND APPARATUS THEREFOR

BACKGROUND OF THE INVENTION

This invention relates to improvements in an ultrasonic measurement method and apparatus for subjecting an object to an ultrasonic transmission and receiving reflected ultrasonic waves from the interior of the object to measure the acoustic characteristics of the object. More particularly, the invention relates to an ultrasonic measurement method and apparatus for measuring, by approximation, attenuation coefficient and reflection coefficient ascribable to propagation of ultrasonic waves internally of an object, thus to obtain information relating to the attenuation and reflection of the ultrasonic waves within the object.

Ultrasonic measurement techniques find application widely in such fields as material testing, SONAR and medical diagnosis. In particular, ultrasound scanner systems for medical purposes have recently been developed.

The principle of operation of an ultrasound scanner apparatus resides in use of a pulse-echo method and utilizes a phenomenon wherein an ultrasonic pulse transmitted into a living body, which is the object undergoing measurement, is reflected at a boundary where there is a difference in acoustic impedance. The reflected wave (echo) is received and processed to display a tomograph of the living body by a so-called B-mode method. Despite the fact that the echo contains a variety of information such as the ultrasonic attenuation, acoustic impedance and propagation velocity of sound, the information utilized at the present time is solely the amplitude of the echo.

More specifically, the propagation velocity of sound in the biological tissue is assumed to be constant and, with regard to attenuation ascribable to ultrasonic propagation, luminance modulation is performed at the value of the echo amplitude arbitrarily corrected by a so-called STC (sensitivity time control) circuit or TGC (time gain control) circuit, with the modulated signal being displayed as a tomograph on a cathode-ray tube. This is referred to as a "B-mode display". Accordingly, the tomograph obtained is nothing more than a qualitative picture of a two-dimensional distribution at a surface where the acoustic impedance is discontinuous, so that the morphological information relating to the position and shape of the biological tissue inevitably forms the core of the information utilized. However, the state of the art is such that information such as that relating to ultrasonic attenuation, which is a characteristic of the biological tissue, is not measured.

Several attempts at attaining attenuation information relating to biological tissue have been reported. However, as will be described below in further detail, an echo waveform contains two types of information, namely attenuation due to propagation through biological tissue, and coefficient of reflection at an interface or boundary where there is a difference in acoustic impedence. Both of these quantities are unknown. Therefore, distinguishing between the effects of these two quantities and recognizing them is extremely difficult at the present time.

If the reflected intensity is assumed to be independent of the frequency of the ultrasonic waves and ultrasonic waves having two or more frequencies are transmitted and the ultrasonic echo received with regard to the same portion of the object under measurement followed by measuring the sound pressure ratio of each frequency component of the echo, then it will be possible to eliminate the influence of the reflected intensity and derive an attenuation coefficient. The foregoing assumption holds in the case of an acoustic interface having a sufficiently wide spread in comparison with the wavelength of the ultrasonic waves, e.g. in the case of a planar reflector. In actuality, however, a scatterer approximately equivalent to or less than the wavelengths used often resides at the biological tissue. It is therefore difficult to consider that the foregoing assumption will always hold for the entirety of a biological tissue.

In addition, if it is assumed that the reflected intensity is approximately constant at a certain portion of a biological tissue, then one may consider that the echo sound pressure ratio across the front and back of this portion of the tissue is proportional to the attenuation coefficient. Further, experiments have been reported wherein an attenuation coefficient is obtained by presupposing a relation giving the frequency dependence of the reflected intensity, transmitting ultrasonic waves having three or more frequencies, receiving the ultrasonic echo with regard to the same portion of the object under measurement, and measuring the sound pressure of each frequency component of the echo, with the attenuation coefficient being obtained from the sound pressure.

Thus, the method employed to isolate and measure an attenuation coefficient in all of the foregoing cases involves making an assumption with regard to the reflected intensity, as well as transmitting and receiving ultrasonic waves having a single frequency component or a plurality of frequency components.

A well-known method of measuring attenuation coefficient relies upon transmission. Specifically, as shown in FIG. 1, a transmitting probe 1 and a receiving probe 2 are disposed so as to confront each other across a specimen 15. If ultrasonic waves are transmitted and received at a frequency f, then the following equation may be obtained giving the relation among the amplitude $V_o(f)$ of the transmitted waves, the amplitude $V_r(f)$ of the received waves, and the attenuation coefficient $\alpha(f,x)$:

$$V_r(f) = V_o(f) \exp\left[ - \int_0^L \alpha(f,x) dx \right]$$

where the attenuation coefficient $\alpha(f,x)$ contains an attenuation coefficient and a forward-scatter coefficient (transmittance). L denotes the total length of the path across the specimen. Taking the natural logarithm of both sides of this equation and transforming gives the following:

$$\ln[V_r(f)/V_o(f)] = - \int_0^L \alpha(f,x) dx$$

Next, by using an X-ray computerized tomographic technique, the projection data may be collected to obtain $\alpha(f,x)$ through use of a well-known filtered back-projection algorithm, by way of example.

However, a problem is encountered in obtaining $\alpha(f,x)$ in this fashion. Specifically, as shown in FIG. 2 by way of example, if a scatterer 3 which exhibits a comparatively high degree of scattering is located at a portion of the specimen 15, there is an apparent decline in the reception amplitude $V_r(f)$ which arrives at the receiving probe 2 (see the graphical representation on the right-hand side of FIG. 2). As a result, the reconstructed picture of the attenuation coefficient distribution displayed on the display unit will give one the impression that a large attenuation coefficient exists at the boundary of the scatterer 3. In other words, the attenuation coefficient, rather than being a pure attenuation coefficient, is instead clearly influenced by the scattering intensity of the scatterer.

SUMMARY OF THE INVENTION

An object of the present invention is to provide an ultrasonic measurement method and apparatus free of the foregoing drawbacks encountered in the prior art.

Another object of the present invention is to provide an ultrasonic measurement method and apparatus through which the attenuation and reflection (scattering) of ultrasonic waves internally of an object under investigation can be measured accurately for practical usage.

According to the present invention, the foregoing objects are attained by providing an ultrasonic measurement method for measuring the acoustic characteristics of an object under investigation by transmitting ultrasonic pulses into the object and detecting an ultrasonic echo signal reflected from within the object. The method includes a first detection step of transmitting ultrasonic pulses into the object from a first direction and detecting an ultrasonic echo signal reflected from within the object, a second detection step of transmitting ultrasonic pulses into the object from a second direction opposite to the first direction and detecting an ultrasonic echo signal reflected from within the object, and a computation step of identifying echo signals, which relate to a desired region of the object, from the echo signals obtained in the first and second detection steps, and calculating the acoustic characteristics of the region from the identified echo signals.

According to a first characterizing feature of the invention, the acoustic characteristics include an ultrasonic attenuation coefficient.

According to another characterizing feature of the invention, the computation step includes calculating an attenuation coefficient of the desired region based on a ratio between echo signals detected in the first detection step for two boundaries of the region, and a ratio between echo signals detected in the second detection step for two boundaries of the region.

Further, according to the invention, the acoustic characteristics include the reflection coefficient of the ultrasonic waves, and the computation step includes calculating the reflection coefficient from the desired region based on the calculated attenuation coefficient.

According to another aspect of the invention, the first and second detection steps are performed using a plurality of measurement directions relative to the object under investigation, and the computation step includes calculating the acoustic characteristics using a mean value of results obtained for the plurality of measurement directions.

The present invention further provides an ultrasonic measurement apparatus for measuring the acoustic characteristics of an object under investigation by transmitting ultrasonic pulses into the object and detecting an ultrasonic echo signal reflected from within the object. The apparatus comprises ultrasonic transceiving means for transmitting ultrasonic pulses into the object from a first direction and detecting an ultrasonic echo signal reflected from within the object, and for transmitting ultrasonic pulses into the object from a second direction opposite to the first direction and detecting an ultrasonic echo signal reflected from within the object, arithmetic means for identifying echo signals, which relate to a desired region of the object, from the echo signals detected by the ultrasonic transceiving means, and for calculating the acoustic characteristics of the region from the identified echo signals, and display means for displaying the calculated acoustic characteristics in the form of a visible picture corresponding to the desired region.

According to the invention, the acoustic characteristics include an ultrasonic attenuation coefficient.

According to another feature of the invention, the acoustic characteristics include the reflection coefficient of the ultrasonic waves.

The ultrasonic transceiving means includes scanning means for scanning the object under investigation in a direction which is substantially perpendicular to the first direction, and the arithmetic means includes memory means for storing echo signals detected by the scanning. The arithmetic means is adapted to identify echo signals at two boundaries of each of a plurality of sections obtained by subdividing a cross-section of the region of interest formed, by the aforementioned scanning, from the echo signals stored in the memory means, and to calculate at least one of an ultrasonic attenuation coefficient and reflection coefficient of each section from the identified echo signals. The display means displays at least the calculated attenuation coefficient or calculated reflection coefficient of each section in the form of a distribution image thereof in the cross-section.

The ultrasonic transceiving means scans the object from a plurality of measurement directions relative to the object, and the arithmetic means calculates acoustic characteristics using a mean value of results obtained for the plurality of measurement directions.

Other features and advantages of the present invention will be apparent from the following description taken in conjunction with the accompanying drawings, in which like reference characters designate the same or similar parts throughout the figures thereof.

BRIEF DESCRIPTION OF THE DRAWINGS

FIGS. 4 through 9 are views useful in describing the principle of the present invention;

DESCRIPTION OF THE PREFERRED EMBODIMENTS

Before describing embodiments of the invention in detail, the theoretical background of the invention will be discussed starting with FIG. 3.

Figure 3:
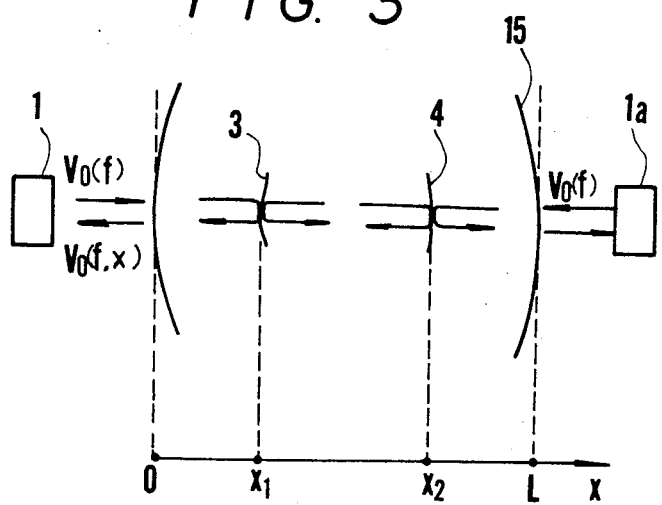
FIG. 3 is a schematic view useful in describing the principle of an ultrasonic measurement method according to the present invention.

In FIG. 3, a probe 1 disposed at the left of a living body 15 under examination is adapted to transmit an ultrasonic pulse $V_o(f)$ into the body. Echos are formed by surfaces 3, 4 where the acoustic impedance is discontinuous. These surfaces shall be referred to as "discontinuity surfaces" where appropriate. The echos are received by the probe 1 as reflected waves of amplitude $V(f,x)$ expressed by equations (1), (2) given below.

First, the amplitude $V(f,x_1)$ at the discontinuity surface 3 is expressed as follows:

$$V(f,x_1) = V_o(f)R(f,x_1)\exp\left[-2\int_0^{x_1}\alpha(f,x)dx\right]T_o^{x_1}(f)T_{x_1}^o(f) \quad (1)$$

where f is the frequency of the ultrasonic waves, $R(f,x_1)$ represents the reflection coefficient, namely the backward scattering intensity, of the discontinuity surface 3, $\alpha(f,x)$ stands for the ultrasonic attenuation coefficient from the skin of the living body (x=0) to the discontinuity surface 3 ($x=x_1$), and $T_o^{x_1}(f)$, $T_{x_1}^o(f)$ represent the product of the transmission coefficients (forward scattering coefficients) from 0 to $x_1$ and from $x_1$ to 0, respectively.

Likewise, the amplitude of the echo from the discontinuity surface 4 ($x=x_2$) is expressed by the following:

$$V(f,x_2) = V_o(f)R(f,x_2)\exp\left[-2\int_0^{x_2}\alpha(f,x)dx\right]T_o^{x_2}(f)T_{x_2}^o(f) \quad (2)$$

Dividing Eq. (1) by Eq. (2) gives the following:

$$V(f,x_1)/V(f,x_2) = R(f,x_1)/R(f,x_2)\cdot\exp\left(-2\int_0^{x_1}\alpha(f,x)dx + 2\int_0^{x_2}\alpha(f,x)dx\right)\cdot\frac{T_o^{x_1}(f)\cdot T_{x_1}^o(f)}{T_o^{x_2}(f)\cdot T_{x_2}^o(f)} \quad (3)$$

$$= R(f,x_1)/R(f,x_2)\cdot\exp\left(2\int_{x_1}^{x_2}\alpha(f,x)dx\right)\cdot\frac{T_o^{x_1}(f)\cdot T_{x_1}^o(f)}{T_o^{x_2}(f)\cdot T_{x_2}^o(f)}$$

$$\because \int_0^{x_2}\alpha(f,x)dx = \int_0^{x_1}\alpha(f,x)dx + \int_{x_1}^{x_2}\alpha(f,x)dx$$

Taking the natural logarithm of both sides of Eq. (3) allows us to write the following:

$$\ln[V(f,x_1)/V(f,x_2)] = \quad (4)$$

$$\ln[R(f,x_1)/R(f,x_2)] + 2\int_{x_1}^{x_2}\alpha(f,x)dx + \ln[1/T_{x_1}^{x_2}(f)T_{x_2}^{x_1}(f)]$$

$$\because [T_o^{x_1}(f)/T_o^{x_2}(f)] = [T_o^{x_1}(f)/T_o^{x_1}(f)\cdot T_{x_1}^{x_2}(f)] = [1/T_{x_1}^{x_2}(f)]$$

If the reflection coefficient within the living body 15 is independent of location and substantially constant, that is, if the relation $R(f,x_1)\simeq R(f,x_2)$ holds, and if the transmission coefficient is close to unity, that is, if the relation $T_o^x(f)\simeq 1$ holds, then, from Eq. (4), $\alpha(f,x)$ can be obtained through use of the following equation:

$$\int_{x_1}^{x_2}\alpha(f,x)dx = \tfrac{1}{2}\ln[V(f,x_1)/V(f,x_2)] \quad (5)$$

Since the attenuation coefficient for soft biological tissue is substantially proportional to the frequency f, we may write $\alpha(f,x)=\alpha(x)\cdot f$. Further, if the mean value of the attenuation coefficient between $x_1$ and $x_2$ is $\bar{\alpha}_{x1x2}$, then we have the following:

$$\int_{x_1}^{x_2}\alpha(f,x)dx = f\int_{x_1}^{x_2}\alpha(x)dx = f\bar{\alpha}_{x1x2}\cdot(x_2-x_1)$$

so that $\bar{\alpha}_{x1x2}$ may be obtained as follows from Eq. (5):

$$\bar{\alpha}_{x1x2} = \frac{1}{2f}\cdot\frac{1}{(x_2-x_1)}\ln[V(f,x_1)/V(f,x_2)] \quad (6)$$

While the foregoing assumptions may have some possibility of holding true for minute portions of the living body 15 that are very close together, there is almost no likelihood that the assumptions will hold for the entirety of a biological tissue.

Let us now consider a case where a measurement is performed in accordance with Eq. (4) for two different frequencies $f_1$ and $f_2$. If we assume that $R(f,x)$, $T(f)$ are independent of frequency, i.e., that $R(f,x)$ is $R(x)$, then, with regard to Eq. (4), the following equations (7), (8) are obtained:

$$\ln[V(f_1,x_1)/V(f_1,x_2)] = \quad (7)$$

$$\ln[R(x_1)/R(x_2)] + 2 \int_{x_1}^{x_2} \alpha(f_1,x)dx + \ln[1/T_{x_1}^{x_2} \cdot T_{x_2}^{x_1}]$$

$$\ln[V(f_2,x_1)/V(f_2,x_2)] = \quad (8)$$

$$\ln[R(x_1)/R(x_2)] + 2 \int_{x_1}^{x_2} \alpha(f_2,x)dx + \ln[1/T_{x_1}^{x_2} \cdot T_{x_2}^{x_1}]$$

Subtracting Eq. (8) from Eq. (7) gives us:

$$\ln\left[\frac{V(f_1,x_1)}{V(f_1,x_2)} \Big/ \frac{V(f_2,x_1)}{V(f_2,x_2)}\right] = 2 \int_{x_1}^{x_2} [\alpha(f_1,x) - \alpha(f_2,x)]dx \quad (9)$$

If $\alpha(f,x) = \alpha(x) \cdot f$ holds and the mean value of $\alpha(x)$ between $x_1$ and $x_2$ is $\bar{\alpha}_{x_1x_2}$, then we may write:

$$\int_{x_1}^{x_2} [\alpha(f_1,x) - \alpha(f_2,x)]dx =$$

$$(f_1 - f_2) \int_{x_1}^{x_2} \alpha(x)dx = (f_1 - f_2)(x_2 - x_1)\bar{\alpha}_{x_1x_2}$$

We therefore have the following:

$$\bar{\alpha}_{x_1x_2} = \frac{1}{2(f_1 - f_2)} \cdot \frac{1}{(x_2 - x_1)} \left[\ln\left\{\frac{V(f_1,x_1)}{V(f_1,x_2)} \Big/ \frac{V(f_2,x_1)}{V(f_2,x_2)}\right\}\right] \quad (10)$$

by which $\bar{\alpha}_{x_1x_2}$ is obtained.

The foregoing assumption will hold true for a boundary or interface having a spread which is sufficiently large in comparison with the wavelength of the ultrasonic waves, e.g., a planar reflector. However, since scatterers which scatter waves on the order of or less than the wavelength used also exist in actual biological tissue, the assumption will not necessarily hold for the entirety of a biological tissue.

According to the present invention, the attenuation coefficient $\alpha(f,x)$ is obtained without relying upon assumptions of the kind described above. According to a feature of the present invention, pulses of amplitude $V_o(f)$ are transmitted into the same living body 15 in a similar fashion from both the probe 1 and a probe 1a arranged to substantially diametrically oppose the probe 1, as shown in FIG. 3. The echos of the ultrasonic pulses from the probe 1a reflected at the discontinuity surfaces 4, 3 within the living body 15 are expressed by respective equations (11), (12) given below. Specifically, if we let L represent the thickness of the living body 15 on the straight line connecting the probes 1, 1a, the discontinuity surfaces 3, 4 will be located at positions indicated by $L-x_1$, $L-x_2$, respectively. Then, by using a modified form of Eq. (1), we obtain equations (11), (12) indicative of the echos for the discontinuity surfaces 4, 3, respectively:

$$V(f, L - x_2) = V_o(f) \cdot R(f, L - x_2) \cdot \exp\left(-2 \int_L^{L-x_2} \alpha(f, x)dx\right) \cdot T_L^{L-x_2}(f) \cdot T_{L-x_2}^L(f) \quad (11)$$

$$V(f, L - x_1) = V_o(f) \cdot R(f, L - x_1) \exp\left(-2 \int_L^{L-x_1} \alpha(f, x)dx\right) \cdot T_L^{L-x_1}(f) \cdot T_{L-x_1}^L(f) \quad (12)$$

Dividing Eq. (11) by Eq. (12) and then taking the natural logarithm of both sides, as in the case of the echo signals received by the probe 1, results in the following equations:

$$\ln[V(f, L - x_2)/V(f, L - x_1)] = \ln[R(f, L - x_2)/R(f, \quad (13)$$

$$L - x_1)] + 2 \int_{x_2}^{x_1} \alpha(f, x)dx + \ln[1/T_{x_2}^{x_1}(f) \cdot T_{x_1}^{x_2}(f)]$$

$$\therefore -2 \int_L^{L-x_2} \alpha(f, x)dx + 2 \int_L^{L-x_1} \alpha(f, x)dx$$

$$= -2 \int_L^{L-x_2} \alpha(f, x)dx + 2 \int_L^{L-x_2} \alpha(f, x)dx + 2 \int_{x_2}^{x_1} \alpha(f, x)dx$$

$$= 2 \int_{x_2}^{x_1} \alpha(f, x)dx$$

Here we can write $$\int_{x_1}^{x_2} \alpha(f, x)dx = \int_{x_2}^{x_1} \alpha(f, x)dx.$$

In other words, the integrated value of the attenuation coefficient over the interval bounded by $x_1$, $x_2$ may be considered to be independent of the direction of ultrasonic propagation. We therefore obtain the following equation:

$$\ln[V(f, L - x_2)/V(f, L - x_1)] = \ln[R(f, L - x_2)/R(f, \quad (14)$$

$$L - x_1)] + 2 \int_{x_1}^{x_2} \alpha(f, x)dx + \ln[1/T_{x_2}^{x_1}(f) \cdot T_{x_1}^{x_2}(f)]$$

Adding Eqs. (4) and (14) gives us the following:

$$\ln\left(\frac{V(f, x_1)}{V(f, x_2)} \cdot \frac{V(f, L - x_2)}{V(f, L - x_1)}\right) = \quad (15)$$

-continued $$\ln\left(\frac{R(f, x_1)}{R(f, x_2)} \cdot \frac{R(f, L - x_2)}{R(f, L - x_1)}\right) +$$

$$4 \int_{x_1}^{x_2} \alpha(f, x)dx + \ln[1/T_{x_1}^{x_2}(f)^2 \cdot T_{x_2}^{x_1}(f)^2]$$

Here, $R(f,x_1)$, $R(f,L-x_1)$ are the reflection coefficients at either side of the discontinuity surface 3, while $R(f,x_2)$, $R(f,L-x_2)$ are the reflection coefficients at either side of the discontinuity surface 4. As shown in FIG. 4, media having acoustic impedances of $Z_1$, $Z_2$ adjoin each other and form a discontinuity surface having the shape of a planar reflector. Letting $V_i$ represent an amplitude of an incident ultrasonic wave, $V_r$ an amplitude of a reflected ultrasonic wave, $\theta_i$ the angles of incidence and reflection and $\theta_t$ the angle of transmission, we may write the relation between the reflection coefficients and $\theta_i$, $\theta_t$ in the manner shown below. Note that R is the reflection coefficient for the case where the ultrasonic wave is incident upon the discontinuity surface from the side $Z_1$, while R' is the reflection coefficient for the case where the ultrasonic wave is incident upon the discontinuity surface from the side $Z_2$. Thus, R and R' are written as follows:

$$R = Vr/Vi = \frac{Z_2 \cos \theta i - Z_i \cos \theta t}{Z_2 \cos \theta i + Z_1 \cos \theta t}$$

$$R' = Vi/Vr = \frac{Z_1 \cos \theta t - Z_2 \cos \theta i}{Z_1 \cos \theta t + Z_2 \cos \theta i}$$

$$|R| = |R'|$$

Further, if the biological tissue of the living body 15 consists of random scatterers, as shown in FIG. 5, that is, if the discontinuity surfaces 3, 4 consist of random scatterers, then the backward scattering coefficients $R(f,x)$ should be equal regardless of the direction in which the ultrasonic waves are propagated and reflected (scattered). This allows us to write $R(f,x) \simeq R(f,L-x)$, or $R(f,x)/R(f,L-x) \simeq 1$.

Accordingly, the first term on the right side of Eq. (15) becomes zero. In other words, we may write:

$$\ln\left(\frac{R(f, x_1)}{R(f, L - x_1)} \cdot \frac{R(f, L - x_2)}{R(f, x_2)}\right) = \ln[1] = 0$$

In addition, $T_{x_1}{}^{x_2}(f)$ and $T_{x_2}{}^{x_1}(f)$ are the transmission coefficients from $x_1$ to $x_2$ and from $x_2$ to $x_1$, respectively. Though there is as yet no correct data regarding the transmission coefficient of soft biological tissue, we can take the following approach. Specifically, it is known that the mean acoustic impedance of soft biological tissue is $1.63 \times 10^6$ (kg/m$^2$ s), and that the acoustic impedance ranges roughly between $1.4 \times 10^6$ and $1.7 \times 10^6$ (kg/m$^2$ s). We may investigate the value of the transmission coefficient by using a model of a planar layer. Thus, as shown in FIG. 6, assume that the ultrasonic waves impinge at substantially right angles on the interface between the two adjoining media having the acoustic impedances of $Z_1$, $Z_2$. Since $\cos \theta_i \simeq \cos \theta_t \simeq 1$ will hold, we have the following:

$$T_{12} = 1 - R = \frac{2Z_2}{Z_1 + Z_2}$$

$$T_{21} = 1 - R' = \frac{2Z_1}{Z_1 + Z_2}$$

$$\therefore T_{12} \cdot T_{21} = \frac{4Z_1Z_2}{(Z_1 + Z_2)^2} = \frac{4\left(\frac{Z_2}{Z_1}\right)}{\left(1 + \frac{Z_2}{Z_1}\right)^2}$$

Figure 7:
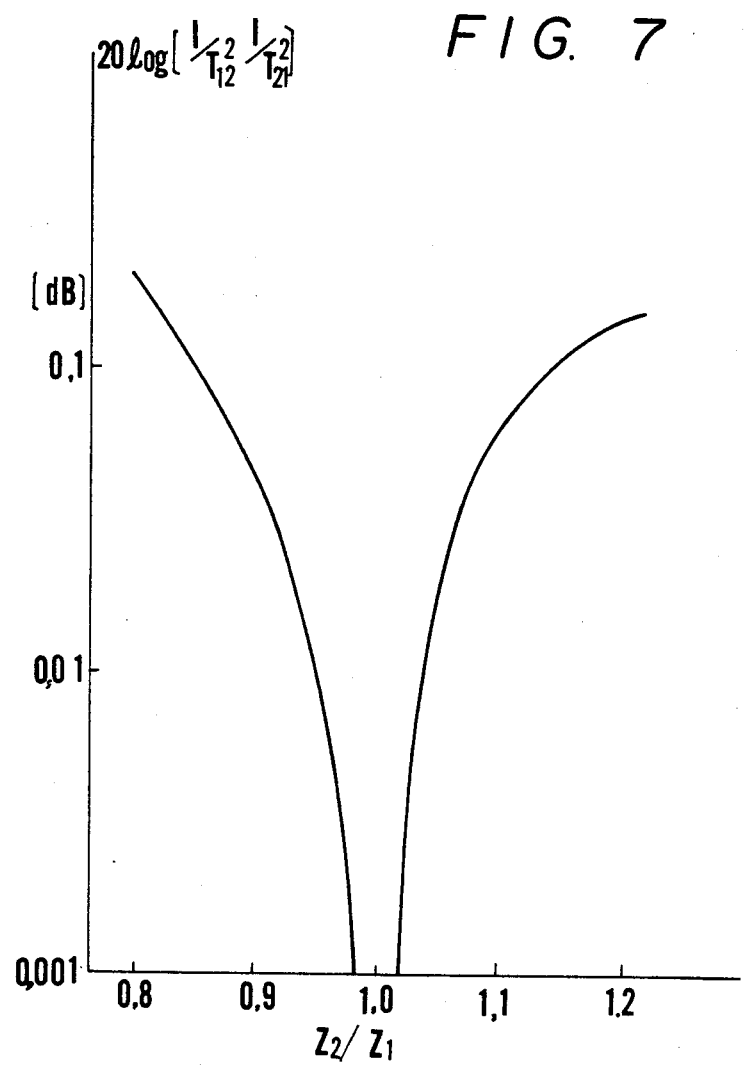

Since the acoustic impedance of soft biological tissue ranges from $1.4 \times 10^6$ to $1.7 \times 10^6$ (kg/m$^2$ s), as mentioned above, $T_{12}T_{21}$ takes on a maximum value when $Z_1 = Z_2$ holds within the above range. Further, when $Z_1 = 1.4 \times 10^6$ (kg/m$^2$ s) and $Z_2 = 1.7 \times 10^6$ (kg/m$^2$ s), we will have $(Z_2/Z_1) = (1.7/1.4) = 1.214$, $T12.T21 = 0.991$, $\ln [1/T_{12}{}^2 \cdot T_{21}{}^2] = 0.019$. Applying a dB conversion in the form of $20 \log [1/T_{12}{}^2 \cdot T_{21}{}^2]$ gives us 0.163 dB. In actuality, the difference in acoustic impedance may be considered small in terms of mean values. In other words, assuming that $Z_1 = 1.5$, $Z_2 = 1.6$ hold, we have $Z_2/Z_1 = 1.06$, so that $\ln [1/T_{12}{}^2 \cdot T_{21}{}^2] = 0.002$. Applying a dB conversion givrs 0.018 dB. FIG. 7 shows the result of calculating the relation between $Z_2/Z_1$ and $20 \log[1/T_{12}{}^2 \cdot T_{21}{}^2]$.

Meanwhile, it is known that the attenuation coefficient of soft biological tissue ranges roughly between 0.5 and 2.0 dB/cm MHz. The range is from 1.5 to 6.0 dB/cm for 3 MHz, which is the frequency band ordinarily used in examining a living body. Accordingly, if the attenuation coefficient and transmission coefficient per centimeter are compared, the latter can be considered to be 1/10 to 1/100 the magnitude of the former, or even smaller. If the attenuation coefficient per millimeter is 0.15 to 0.6 dB/mm and the relation $0.86 \leq Z_2/Z_1 \leq 1.17$ holds from FIG. 7, then the transmission coefficient can be considered to be about 1/10 the attenuation coefficient or smaller. Therefore, with respect to soft biological tissue having a mean acoustic impedance of $1.63 \times 10^6$ (kg/m$^2$ s), the transmission coefficient of soft tissue for an acoustic impedance ranging from $1.4 \times 10^6$ to $1.9 \times 10^6$ (kg/m$^2$ s) can be estimated to be about 1/10 of the attenuation coefficient or less.

A well-defined theory for calculating the actual transmission coefficient (forward scattering coefficient) of soft biological tissue has not yet been established. However, when the difference in acoustic impedance is considered to be very small, the transmission coefficient can be expected to come quite close to unity and may be assumed to be negligible in comparison with the attenuation coefficient. In the event that the transmission coefficient is not neglible with respect to the attenuation coefficient, then this will appear in the attenuation coefficient as an error. Tables I and II indicate values of acoustic impedance and attenuation coefficients for biological tissue.

TABLE I

| Biological Tissue | Acoustic Impedance ($\times 10^5$g/cm$^2$ sec) |
|---|---|
| Fat | 1.38 |
| Aqueous humour of eye | 1.50 |
| Vitreous humour of eye | 1.52 |
| Brain | 1.58 |
| Blood | 1.61 |
| Kidney | 1.62 |
| Human tissue | 1.63 |

TABLE I-continued

| Biological Tissue | Acoustic Impedance ($\times 10^5 \text{g/cm}^2 \text{sec}$) |
|---|---|
| (mean value) | |
| Spleen | 1.64 |
| Liver | 1.65 |
| Muscle | 1.70 |
| Lens of eye | 1.84 |
| Skull-bone | 7.80 |

TABLE II

| Tissue | α/f Mean Value (dB/cm MHz) | α/f Standard Deviation (dB/cm MHz) | Frequency Range (MHz) |
|---|---|---|---|
| Aqueous or vitreous humour of eye | 0.10 | — | 6–30 |
| Blood | 0.18 | — | 1.0 |
| Fat | 0.63 | 0.073 | 0.8–7.0 |
| Medulla oblongata along fibres | 0.80 | 0.071 | 1.7–3.4 |
| Brain | 0.85 | 0.056 | 0.9–3.4 |
| Liver | 0.94 | 1.058 | 0.3–3.4 |
| Kidney | 1.0 | 0.04 | 0.3–4.5 |
| Spinal cord | 1.0 | — | 1.0 |
| Medulla oblongata across fibres | 1.2 | 0.05 | 1.7–3.4 |
| Muscle, along fibres | 1.3 | 0.07 | 0.8–4.5 |
| Heart muscle | 1.8 | 0.10 | 0.3–4.5 |
| Lens of eye | 2.0 | — | 3.3–13 |
| Muscle, across fibres | 3.3 | 0.35 | 0.8–4.5 |
| Skull-bone | 20 | — | 1.6 |
| Lung | 41 | — | 1.0 |

On the basis of the foregoing assumption, Eq. (15) may be written as follows:

$$\int_{x_1}^{x_2} \alpha(f, x) dx = \frac{1}{4} \ln \left( \frac{V(f, x_1)}{V(f, x_2)} \cdot \frac{V(f, L - x_2)}{V(f, L - x_1)} \right) \quad (16)$$

Thus, α(f,x) may be obtained from Eq. (16).

Figure 8:
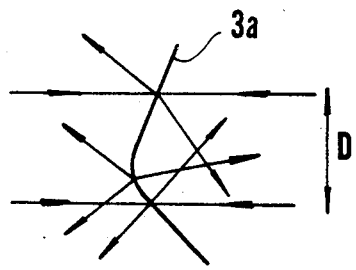

Eq. (16) is the result obtained in a case where a discontinuity surface is composed of random scatterers. Even when the discontinuity surface is not composed of random scatterers, however, it is possible to consider that $R(f,x)/R(f,L-x) \simeq 1$ holds if the discontinuity surface does not change greatly, that is, if the discontinuity surface changes only gradually, within the size of the ultrasonic beam width. However, when a discontinuity surface 3a changes significantly within an ultrasonic beam width D, as shown in FIG. 8, there is a possibility that $R(f,x) \neq R(f,L-x)$ will hold. In such case, it is necessary to devise some means of minimizing the error term $$\ln \left( \frac{R(f, x_1)}{R(f, x_2)} \cdot \frac{R(f, L - x_2)}{R(f, L - x_1)} \right).$$

A detailed discussion in this regard will appear below.

Let us first describe an embodiment for a case where the relation $R(f,x)/R(f,L-x) \sim 1$ is assumed to hold. If the assumption holds true, it will be possible to obtain α(f,x) from Eq. (16). More specifically, the probes 1, 1a are disposed on opposite sides of the living body 15 so as to confront each other, and the echo signals from the discontinuity surfaces at $x_1$, $x_2$ are measured independently by the probes. From the measured echo amplitudes V(f,$x_1$), V(f,$x_2$) and V(f,L−$x_2$), V(f,L−$x_1$), α(f,x) can be calculated using Eq. (16). In this case, however, note must be taken of the fact that the distances from the discontinuity surface 3 to the probes 1, 1a differ. To correct for an ultrasonic wave divergence phenomenon ascribable to this difference in distance, the reflected wave may be considered to be a spherical wave. If the reception surface areas of the probes 1, 1a are the same, a divergence component proportional to the square of the distances can be cancelled by the following equation:

$$\int_{x_1}^{x_2} \alpha(f, x) dx = \frac{1}{4} \ln \left( \frac{V(f, x_1)}{V(f, L - x_1)} \cdot \frac{(L - x_1)^2}{x_1^2} \cdot \frac{V(f, x_2)}{V(f, L - x_2)} \cdot \frac{(L - x_2)^2}{x_2^2} \right) \quad (17)$$

Further, according to the present invention, propagation velocity in human tissue $C_o$ is assumed to be substantially constant (1530 m/S). Accordingly, $x = C_o t$ may be considered to hold and, since $C_o$ is constant, FIG. 17 takes on the following form:

$$\int_{x_1}^{x_2} \alpha(f, x) dx = \frac{1}{4} \ln \left( \frac{V(f, C_o t_1)}{V(f, C_o T - C_o t_1)} \cdot \frac{(T - t_1)^2}{t_1^2} \cdot \frac{V(f, C_o t_2)}{V(f, C_o T - C_o t_2)} \cdot \frac{(T - t_2)^2}{t_2^2} \right) \quad (18)$$

where $L = C_o T$.

Figure 9:
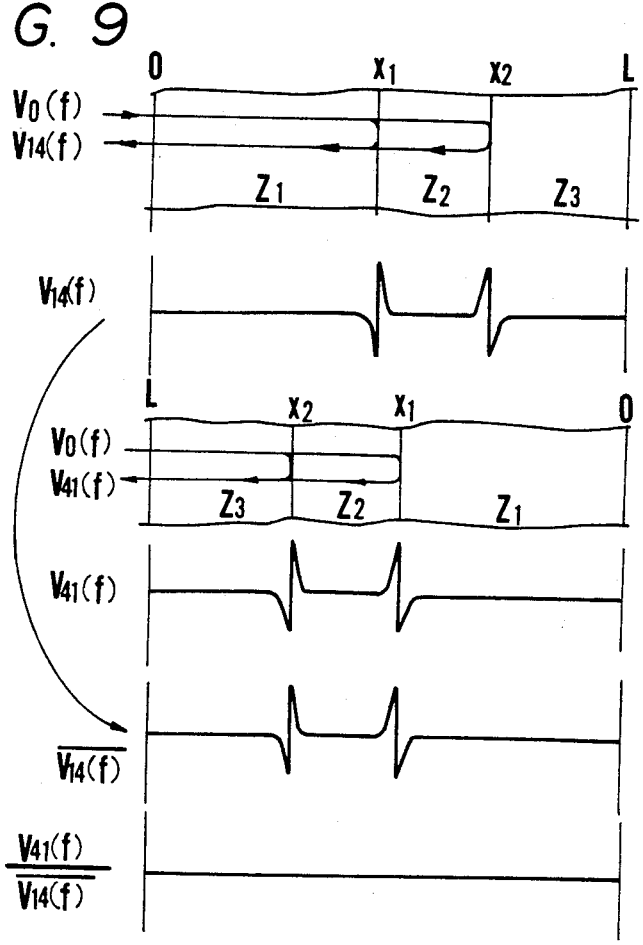

If the propagation velocity $C_o$ of sound is constant, the echo positions from the discontinuity surfaces $x_1$, $x_2$ will coincide provided that an echo $V_{14}(f)$ which results when a transmission is made by the left probe 1, and an echo $V_{41}(f)$ which prevails when a transmission is made from the right probe 1a, are inverted relative to each other in terms of time, as shown in FIG. 9. In other words, a waveform $\overline{V_{14}}(f)$, obtained by inverting the echo $V_{14}(f)$ on its time axis, will be substantially the same as the echo $V_{41}(f)$, as shown in FIG. 9. Therefore, $V_{41}(f)/\overline{V_{14}}(f)$ is substantially equal to unity.

Ordinarily, the sonic pressure from a probe varies according to the distance from the probe and the sound field is particularly complex over a near field. Though the sound field over a far field exhibits a comparatively gentle configuration, it too undergoes variation. For these reasons, it is preferable to use the far field sound for measurement.

Figure 10:
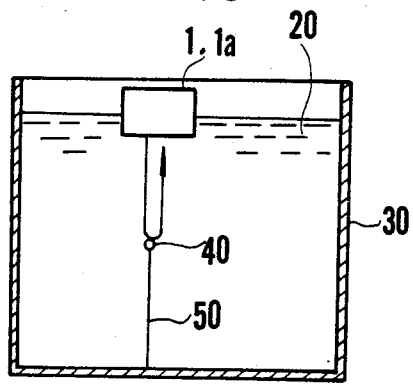
FIGS. 10 and 11 are schematic views useful in describing a method of calibrating an ultrasonic probe.
Figure 11:
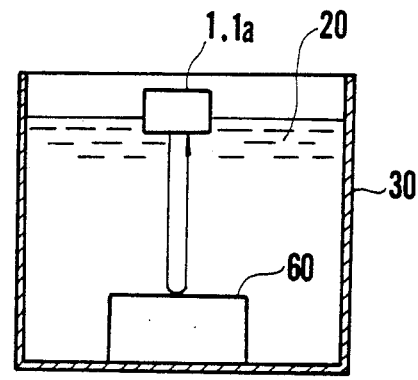

In order to eliminate measurement error ascribable to the change in sound field, it is necessary to measure the sound field characteristics from a standard reflector 40 or 60 submerged in a standard medium 20, as shown in FIG. 10 or FIG. 11, and to normalize the measured value by using the standard sound pressure characteristics. In this way it is possible to simultaneously eliminate the error ascribable to the sound field variation as well as the ultasonic wave divergence error attributable to the distance between the reflectors and probes. FIG. 10 illustrates a case where the standard reflector 40 is a point reflector supported by a support 50. FIG. 11 illustrates a case where the standard reflector 60 is a planar reflector. In either case, a tank 30 is filled with, e.g., degased water serving as the standard medium 20, with the probe 1 or 1a being arranged to measure the sound field characteristics.

When normalization is performed in this manner, if the standard sound field (amplitude) at a distance x is represented by U(f,x), Eq. (16) may be transformed in the following manner to obtain $\alpha(f,x)$, rather than dispensing with the correction of diffusion effected by Eq. (18).

$$\int_{x_1}^{x_2} \alpha(f,x)dx = \quad (19)$$

$$\frac{1}{4} \ln\left[\frac{V(f,x_1)}{V(f,x_2)} \cdot \frac{U(f,x_2)}{U(f,x_1)} \cdot \frac{V(f,L-x_2)}{V(f,L-x_1)} \cdot \frac{U(f,L-x_1)}{U(f,L-x_2)}\right]$$

By obtaining $\alpha(f,x)$, the reflection coefficient R(f,x) can be calculated using Eqs. (4) and (14). The attenuation coefficient of the object under investigation can be ascertained by measuring $\alpha(f,x)$, and R(f,x) may be obtained from the attenuation characteristic and Eq. (4). Specifically, we will have the following equation:

$$\ln[R(f,x_1)/R(f,x_2)] = \ln[V(f,x_1)/V(f,x_2)] - 2\int_{x_1}^{x_2} \alpha(f,x)dx \quad (20)$$

(where the transmission coefficient T is negligible). In other words, an STC correction can be executed in accurate fashion. In addition, R(f,L−x) may be obtained from Eq. (14) in similar fashion. That is, we have the following equation;

$$\ln[R(f,L-x_2)/R(f,L-x_1)] =$$

$$\ln[V(f,L-x_2)/V(f,L-x_1)] - 2\int_{x_1}^{x_2} \alpha(f,x)dx$$

In accordance with the principle of the invention, we have the relation $$\ln[R(f,x_1)/R(f,x_2)] = \ln\left[\frac{1}{R(f,L-x_2)/R(f,L-x_1)}\right]$$

However, though the relative value $R(f,x_1)/R(f,x_2)$ of R(f,x) can be determined, the absolute value thereof cannot. This is because the coefficient $R(f,x_o)$ of reflection from the surface of the object 15 cannot be determined by the initial echo from this surface. As mentioned earlier, however, $R(f,x_o)$ can be obtained by using the standard reflector. That is, the echo amplitude $U(f,x_o)$ of the echo from the standard reflector (e.g., an aluminum planar reflector) at $x_o$ within the degased water is a measured quantity expressed by $U(f,x_o) = V_o(f)R_o(f,x_o)$. It is well known that the reflection coefficient $R_o$ in this case is given by the equation $R_o = (Z_{A1} - Z_o)/(Z_o + Z_{A1})$, where $Z_o$, $Z_{A1}$ are the acoustic impedance of water and aluminum, respectively. $Z_o = 1.48 \times 10^5$ (at a temperature of 20° C.), $Z_{A1} = 18.0 \times 10^5$ (g/cm²s). Accordingly, attenuation of the ultrasonic waves in the degased water is so small as to be negligible. Therefore, $R_o(f,x_o) = 0.848$.

Next, the amplitude $V(f,x_o)$ of the echo from the surface of the object 15 is given by the equation $V(f,x_o) = V_o(f)R(f,x_o)$. From the foregoing two equations we may write the following:

$$R(f,x_o) = R_o(f,x_o)\frac{V(f,x_o)}{U(f,x_o)}$$

The reflection coefficient $R(f,x_o)$ at the surface of the object 15 under investigation obtained in this manner is replaced by $\hat{R}(f,x_o)$. In other words, $\hat{R}(f,x_o) \equiv R(f,x_o)$. If $\hat{R}(f,x)$ is calculated from a quantity obtained by calibrating the echo amplitude V(f,x) by means of U(f,x), then the following can be calculated upon transforming Eq. (20):

$$\frac{\hat{R}(f,x_o)}{\hat{R}(f,x_1)} = \left[\frac{V(f,x_o)}{V(f,x_1)} \cdot \frac{U(f,x_1)}{U(f,x_o)}\right] \exp\left[-2\int_{x_o}^{x_1} \alpha(f,x)dx\right]$$

If $\hat{R}(f,x_o)/\hat{R}(f,x_1) \equiv k_{01}$ holds, then we will have $\hat{R}(f,x_1) = \hat{R}(f,x_o)/k_{01}$. Likewise, we may obtain $\hat{R}(f,x_1)/\hat{R}(f,x_2) = k_{12}$. We therefore have the following:

$$\hat{R}(f,x_2) = \hat{R}(f,x_1)/k_{12} = \hat{R}(f,x_o)/k_{01}k_{12}.$$

In general, the following will hold:

$$\hat{R}(f,x_i) = \hat{R}(f,x_{i-1})/k_{i-1,i}.$$

In other words, the actual reflection coefficient $\hat{R}(f,x_i)$ can be calculated from $\hat{R}(f,x_{i-1})$, which is obtained at the immediately preceding position.

Thus, the reflection coefficient R(f,x) is obtained from the relation among $\alpha(f,x)$, $\hat{R}(f,x_o)$ and Eq. (20).

As described above, the present invention theoretically is effective with respect to regions of the human body through which ultrasonic waves may penetrate. Though the invention is best applied to the breast region, it is also fully applicable to the abdomen.

A first embodiment in which the invention is applied to a breast will now be described in detail with reference to FIGS. 12(a) and (b).

Figure 13:
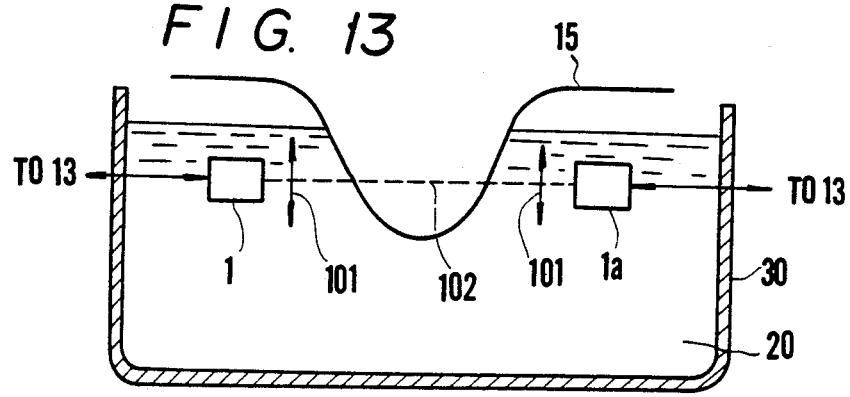
FIGS. 13 and 14 are schematic views useful in describing an example of a breast examination in accordance with the embodiment of FIG. 12.

In order to maintain the natural shape of a breast 15, which is the object under investigation, the patient ordinarily lies face down with the breast suspended within the degased water 20 of the water tank 30 when the examination is performed, as shown in FIG. 13. The probes 1, 1a are interconnected by a connecting arm 18 within the degased water 20 so as to be situated at diametrically opposed points on either side of the breast 15. The probes 1, 1a are capable of being moved and scanned in a vertical direction 101 and in a scanning direction 100 by a scanning mechanism 14 under the control of a controller 8.

A switching circuit 13 is operable to connect the probes 1 or 1a to a transmitting circuit 23 which forms a transmitting system, or to a receiving system composed of such components as a receiving circuit 21, a logarithmic amplifier 22, a detecting circuit 5, a memory circuit 9, and an STC circuit 6.

An ultrasonic echo reflected from within the breast 15 is displayed in the form of a visible image on a display unit 7. What is displayed on the display unit 7 is, e.g., an ultrasonic attenuation coefficient or reflection coefficient of the breast 15 as calculated in accordance with the present invention. The attenuation coefficient or reflection coefficient is obtained from the received ultrasonic echo by an arithmetic unit 11 using two memory circuits 9, 10. At such time, the region of interest (ROI) whose attenuation coefficient or reflection coefficient is to be measured is set by a region-of-interest setting unit 19.

Figure 12:
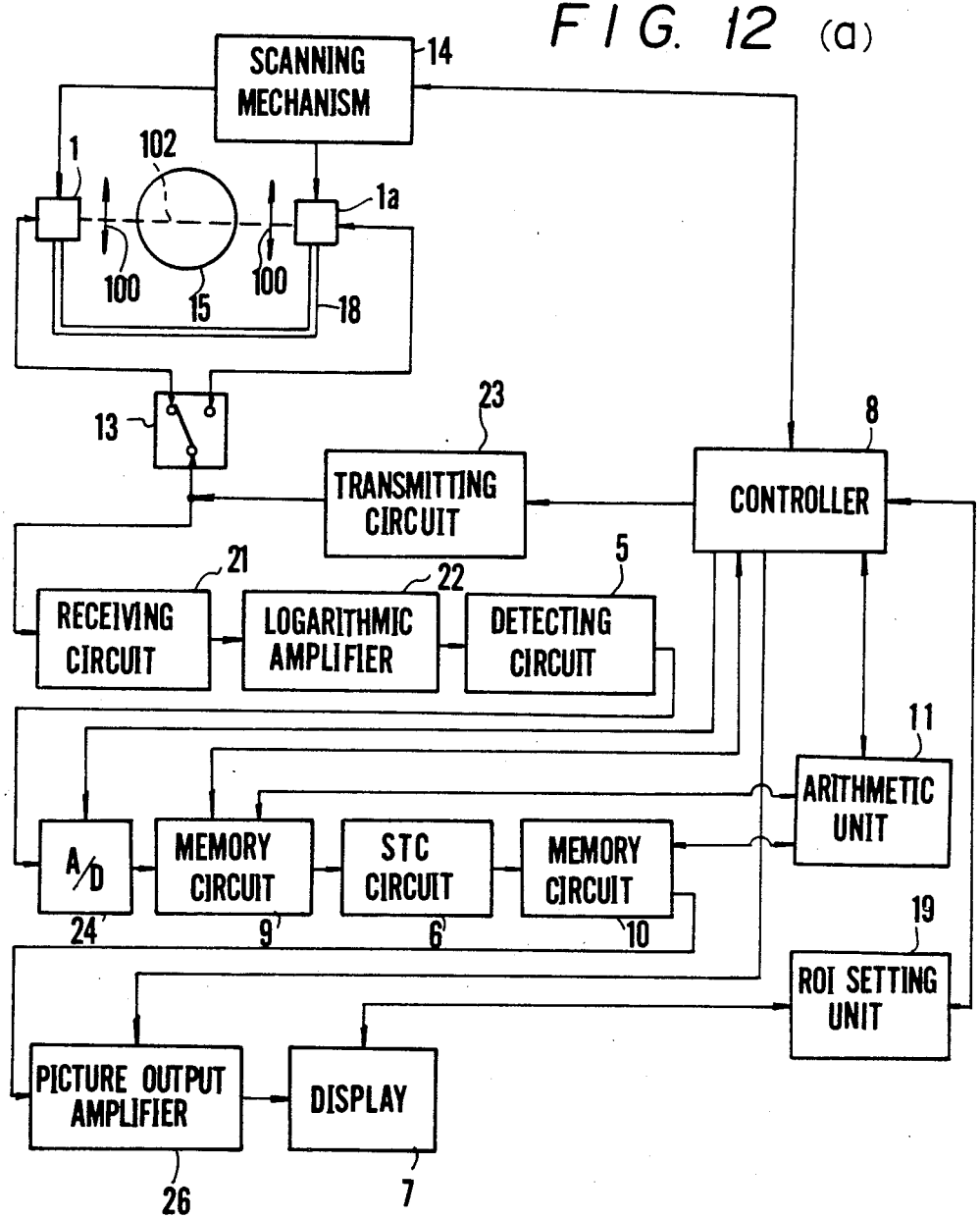
FIGS. 12(a) and (b) are block diagrams illustrating an embodiment of an ultrasonic measurement apparatus according to the present invention.
Figure 12B:
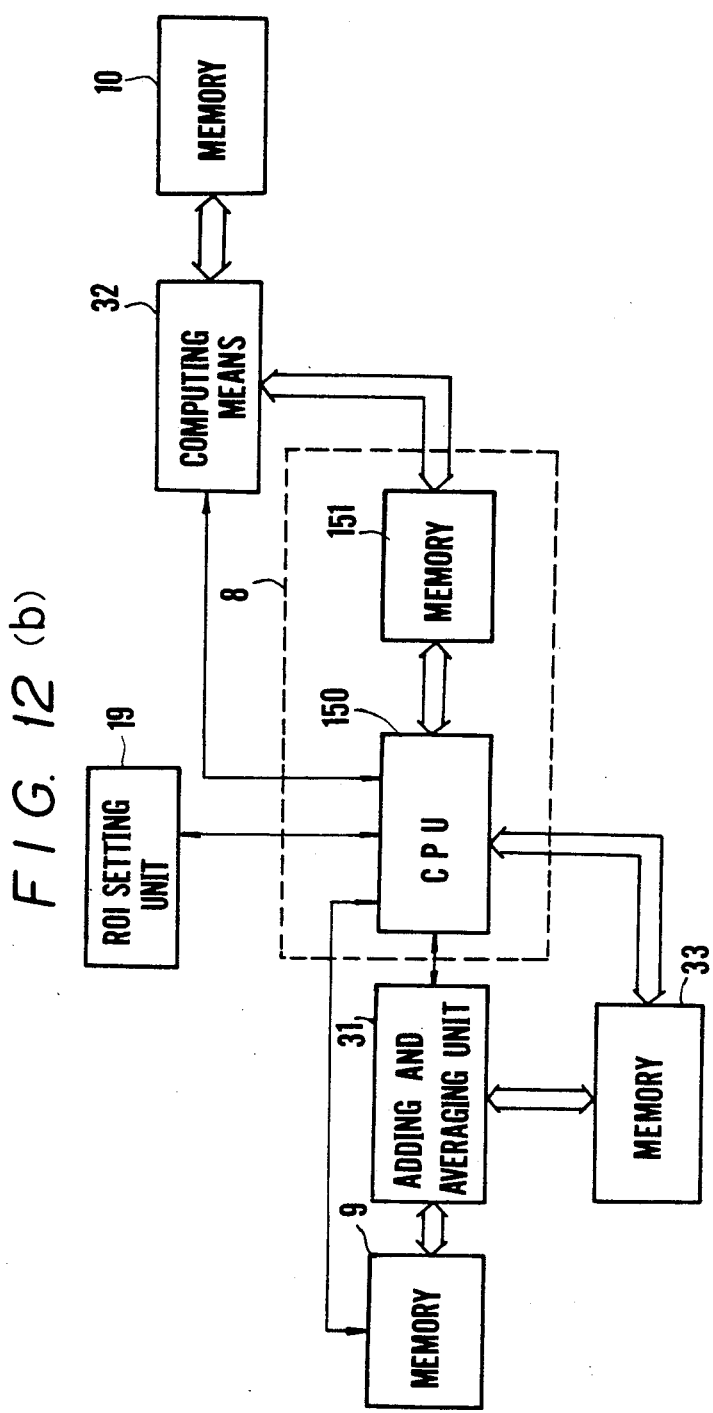

FIG. 12(b) is a block diagram showing the connections among the controller 8, arithmetic unit 11, memory 9, memory 10 and region-of-interest setting unit 19. The units enclosed by the dashed line are the components constituting the controller 8, namely a CPU 150 and a memory 151. The CPU 150, which is a central processing unit of a minicomputer or the like, controls the operation of the ultrasonic measurement apparatus in accordance with a control program stored in the memory 151. The arithmetic unit 11 has an internal memory in which is stored a standard sound pressure value for calibrating a received echo, as described above. The portion for the memory storing the standard sound pressure value may make use of a non-volatile memory.

Figure 19:
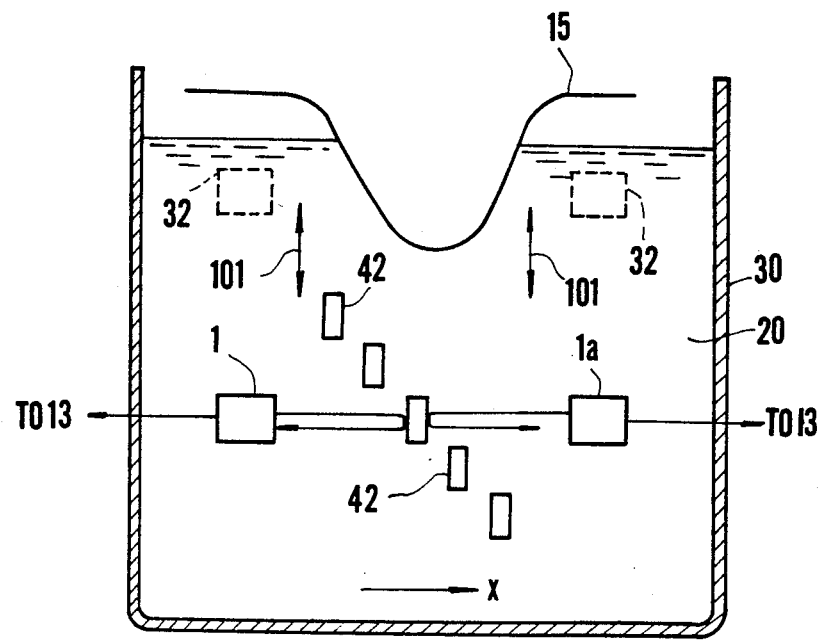
FIG. 19 is a schematic view showing another example of a method of calibrating an ultrasonic probe.

If a plurality of standard reflectors 42 are disposed in an array within the water tank 30, as shown in FIG. 19, then a calibrating scan can be carried out to good advantage even when the probes are exchanged. More specifically, the standard reflectors 42 are arrayed along the scanning direction 101 and staggered along the x direction in the manner shown. Before the probes 1, 1a are disposed at the positions indicated by the dashed lines 32 for the purpose of analyzing the breast 15, they are placed on either side of the array of standard reflectors 42 and scanned along the direction 101 to measure the echos from each of the standard reflectors. The results are stored in the internal memory of the arithmetic circuit 11. When the breast 15 is subsequently subjected to measurement, the measured values are normalized on the basis of these stored standard data.

The procedure for obtaining the conventional B-mode picture will now be described with reference to the flowchart of FIG. 15(a). The program indicated by this flowchart is the control program flowchart stored in the memory 151, as mentioned above.

First, step 1500 in the flowchart calls for setting the height 102 of the cross-section to be scanned. This is done by moving the probes 1, 1a by means of the scanning mechanism 14. Next, in step 1502, the switching circuit 13 selects the probe 1. Step 1504 calls for driving the transmitting circuit 23 and starting an A/D converter 24. The transmitting circuit 23 produces a drive pulse, which actuates the probe (probe 1) selected by the switching circuit 13, whereby an ultrasonic pulse is transmitted toward the breast 15. An echo reflected from within the breast 15 is received by the same probe 1. The echo signal is amplified by the receiving circuit 21 and is then logarithmically compressed and amplified by the logarithmic amplifier 22. The signal is subsequently detected by the detecting circuit 5 and then converted into a digital signal by the A/D converter 24. In step 1506, the digital signal is stored in the memory 9 with every sweep. Next, in order to start the sweep performed by the probe 1a, a decision step 1508 is executed to determine whether a sweep performed by the probe 1a has ended. If the decision is negative (NO), then the probe 1a is selected by the switching circuit 13 in a step 1510, followed by repetition of steps 1504 through 1508. If the decision rendered in step 1508 is YES, namely that the sweep using probe 1a has ended, then the program moves to a step 1509 where a decision is rendered as to whether a full scan has ended.

The end of a full scan is indicated when the scanning mechanism 14 has reached the end of its stroke along the scanning direction 100. If the decision rendered in step 1509 is NO, the program moves to a step 1511, which calls for the scanning mechanism 14 to be provided with a command to transport the probes 1, 1a by one step. This is followed by repetition of steps 1502 through 1509.

Thus, through the foregoing steps, echo signals received by the probes 1, 1a sweep by sweep are stored in the memory 9 one after another upon being converted into digital signals.

At the end of a full scan, the signals stored in the memory 9 are subjected to an attenuation correction by the STC circuit 6 in a step 1512, with the corrected signals being stored in the memory 10. In this case, the signals corrected by the STC circuit 6 are either the echo signals received by the probe 1 or the echo signals received by the probe 1a, the selection being made as desired.

The STC-corrected echo signals are luminance-modulated by a picture output amplifier circuit 26 in a step 1516 and are then displayed as a B-mode picture by the display unit 7 in a step 1517. The picture is of the kind shown in FIG. 14.

Figure 14:
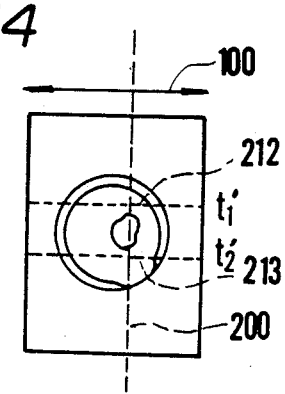

To set a section in which the attenuation coefficient is to be measured using the B-mode picture shown in FIG. 14, the operator uses the region-of-interest setting circuit 19. For example, the set position of an ROI designated by two transverse lines 212, 213, as shown in FIG. 14, is applied to the controller 8. In other words, an interval designated by the two transverse lines 212, 213 in FIG. 14 is grasped as addresses of a pixel demarcated by the region-of-interest setting unit 19 into a rectangular shape on the display unit 7. The pixel addresses have the width indicated by the transverse lines 212, 213. Therefore, if correspondence is established between the pixel addresses and A-mode signals in the memory 9, then the pixel addresses should be A-mode signals corresponding to the i-th to j-th scanning lines. Further, the addresses of a pixel in a direction orthogonal to the scanning direction 100 are given by times $t_1'$, $t_2'$. The CPU 200 thus reads the coordinates i, j, $t_1'$, $t_2'$ of the region of interest into the memory 151 in a step 1518 in the flowchart of FIG. 15(c).

Figure 16:
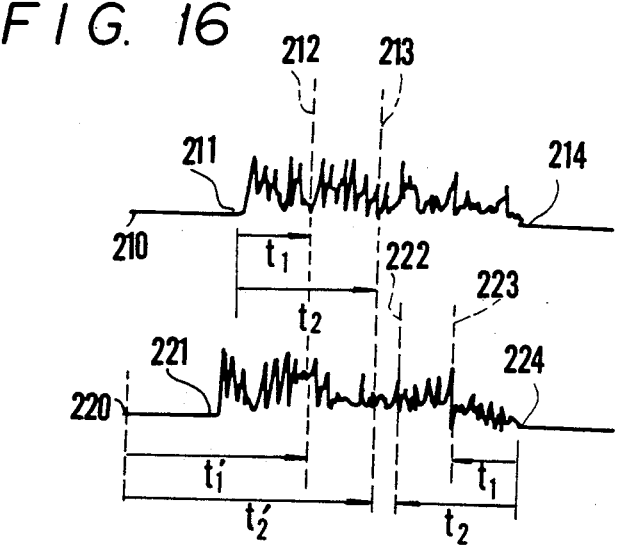
FIG. 16 is a waveform diagram showing an ultrasonic echo waveform useful in describing the flowchart of FIG. 15.

Next, in a step 1520, an adding and averaging operation is performed with regard to the A-mode signals obtained from the probe 1 in the scanning line interval i-j obtained in the step 1518. The mean A-mode signal obtained in this manner is displayed in the form 210 shown in FIG. 16. Likewise, in the next step 1522, an adding and averaging operation is performed with regard to the A-mode signals obtained from the probe 1a in the scanning line interval i-j, and the mean A-mode signal obtained is displayed in the form 220 shown in FIG. 16. The signals 210, 220 are stored in the memory 33 of FIG. 12B. The program then moves to a step 1524, which calls for obtaining a mean amplitude ln $V(f,x_1')$ after time $t_1'$, and a mean amplitude ln $V(f,x_2')$ after time $t_2'$, for the signal 210. Note that $x_1' = C_o t_1'$, $x_2' = C_o t_2'$.

The next step executed is step 1526, in which the position 211 of the breast surface is detected from the signal 210, followed by calculation of times $t_1$, $t_2$ from 211 to 212, 213, respectively. Accordingly, we will have $x_1 = C_o t_1$, $x_2 = C_o t_2$. Next, in a step 1528, a position 224 corresponding to the breast surface 211 is detected from the mean signal 220 obtained from the probe 1a, and mean amplitudes ln V(f,L−x$_1$), ln V(f,L−x$_2$) corresponding to respective positions 223, 222 separated from 224 by the times t$_1$, t$_2$ are fetched. This is followed by a step 1530, in which ln V(f,x$_1$), ln V(f,x$_2$), ln V(f,L−x$_1$), ln V(f,L−x$_2$) are normalized by the above-described standard sound pressure signals ln U(f,x$_1$), ln U(f,x$_2$), ln U(f,L−x$_1$), ln U(f,L−x$_2$). Next, in a step 1532, the mean attenuation coefficient $\bar{a}$ in the interval 212-213 of the ROI is found from each of the values obtained in step 1530.

The mean attenuation coefficient $\bar{a}$ is calculated in the following manner. Since $\alpha(f,x)$ may be considered to be proportional to the frequency f, the relation $\alpha(f,x)=f\alpha(x)$ holds. Accordingly, we have the following:

$$\int_{x_1}^{x_2} \alpha(f,x)dx = f(x_2 - x_1)\bar{\alpha} = f \cdot C_0(t_2 - t_1)\bar{\alpha}$$

Therefore, from Eq. (19), we have the following equation:

$$\bar{\alpha} = \frac{1}{4f} \cdot \frac{1}{C_0(t_2-t_1)} \cdot \qquad (21)$$

$$\ln\left[\frac{V(f,x_1)}{V(f,x_2)} \cdot \frac{U(f,x_2)}{U(f,x_1)} \cdot \frac{V(f,L-x_2)}{V(f,L-x_1)} \cdot \frac{U(f,L-x_1)}{U(f,L-x_2)}\right]$$

We thus obtain the mean attenuation coefficient $\bar{\alpha}$ within a specific interval (the interval of the ROI). The mean attenuation coefficient $\bar{\alpha}$ obtained in this fashion is stored in the memory 10 (step 1534).

Figure 15:
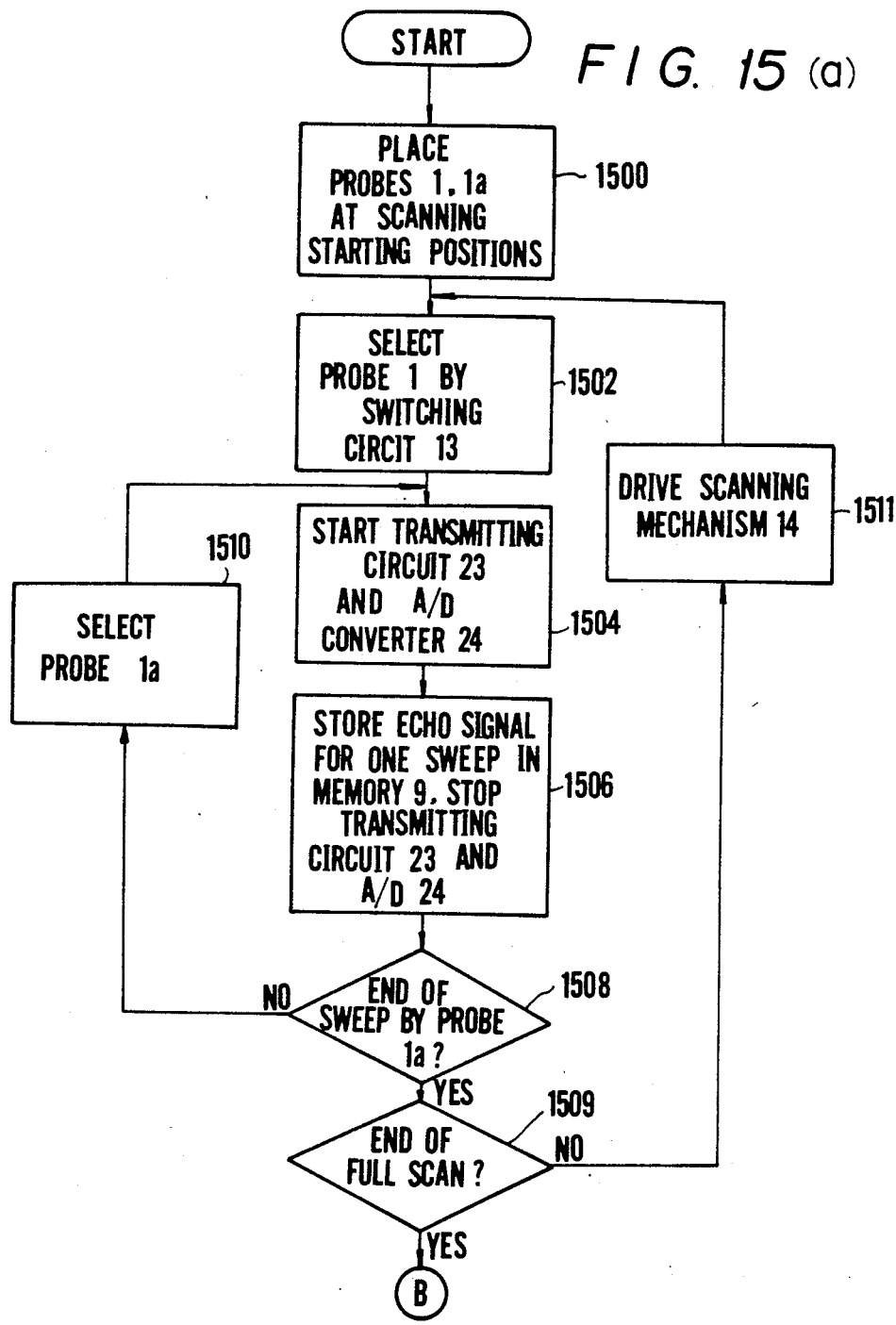
FIGS. 15(a), (b) and (c) are flowcharts illustrating an ultrasonic attenuation coefficient calculation executed by a control unit in the embodiment of FIG. 12.
Figure 15:
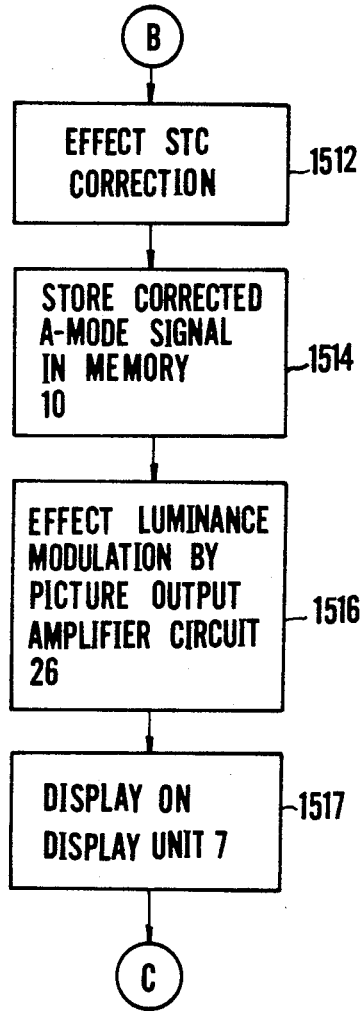
Figure 15C:
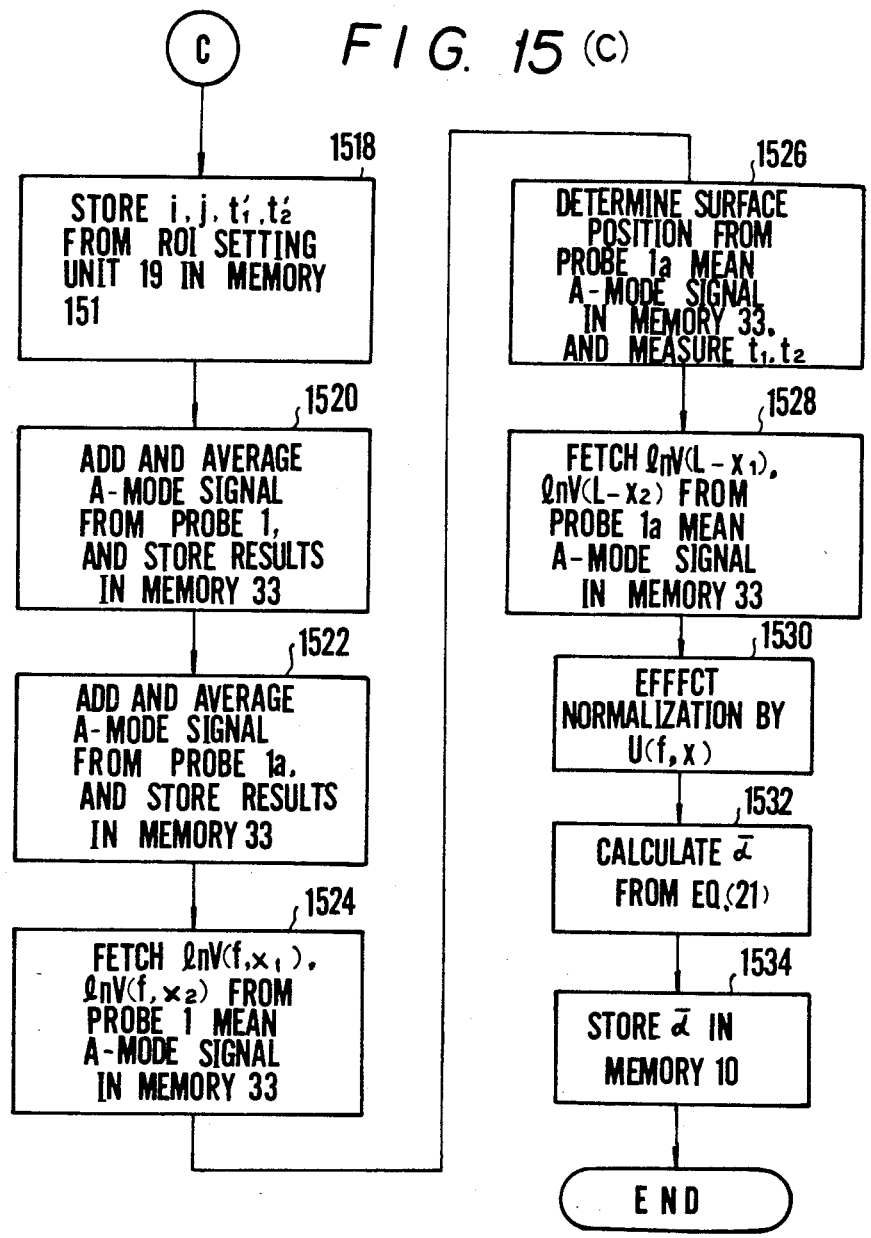
Figure 22:
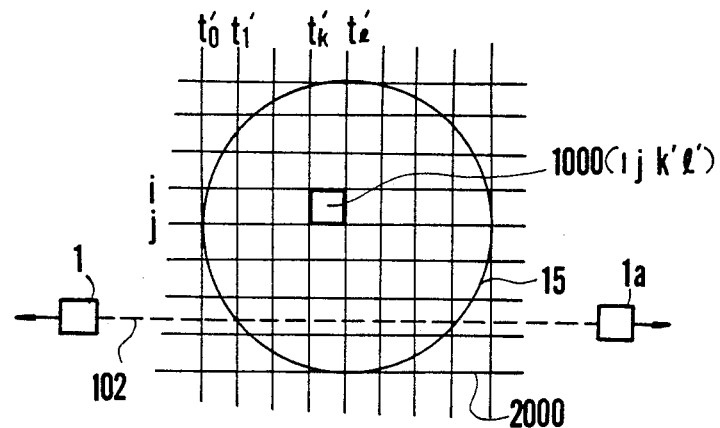
FIGS. 22 through 24 are views useful in describing an operation for displaying measured acoustic characteristics as a picture of a distribution.

Described next will be a method of obtaining the distribution of the mean attenuation coefficient $\bar{\alpha}$ of the object under investigation. To facilitate the understanding of the method, the distribution will be obtained by regarding the ROI interval as a small pixel. That is, as shown in FIG. 22, the measured region of the object 15 is divided into a virtual matrix 2000, a measurement similar to that described in connection with FIG. 12 is performed with respect to each of the pixels 1000 constituting the matrix components, and the attenuation coefficient $\bar{\alpha}(f,x_{ijkl})$ of each pixel 1000 is obtained. The algorithm represented by steps 1518 through 1534 of FIG. 15 is applied for each pixel 1000(ijk'l') bounded by scanning lines i, j and times $t_k'$, $t_l'$. It will be appreciated that if $t_1'$, $t_2'$, $t_1$, $t_2$ of FIG. 15 are considered to be $t_k'$, $t_l'$, $t_k$, $t_l$ in FIGS. 22 and 23, then $\bar{\alpha}(f,x_{ijkl})$ may be obtained exactly as set forth above in conjunction with FIG. 15.

Figure 23:
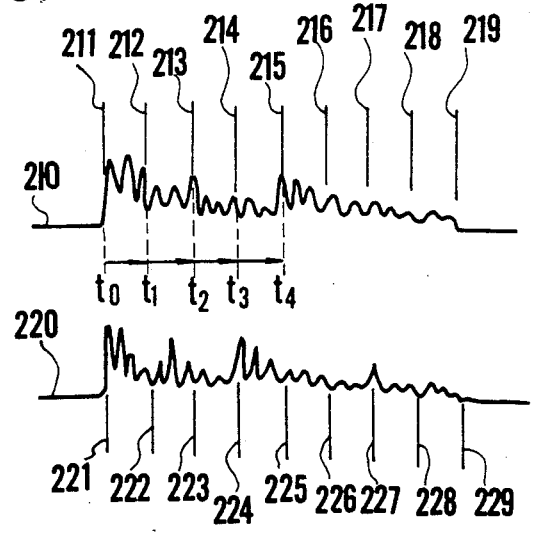
Figure 24:
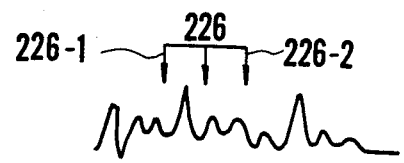

We shall assume that the signals 210, 220 shown in FIG. 23 are those obtained by taking the mean of the A-mode signals from scanning line numbers i through j. In addition, by way of example, 227 is an echo signal received by the probe 1a and corresponding to the echo signal 213 received by the probe 1. Further, the counterpart of the signal 214 is a signal 226. These four signals 213, 214 and 227, 226 correspond to V(f,x$_1$), V(f,x$_2$) and V(f,L−x$_2$), V(f,L−x$_1$) of Equation 15, respectively. In actuality, the amplitude giving V(f,x) is measured as the mean value of a signal having a predetermined duration with respect to the position of the signal. In other words, as shown in FIG. 24, with regard to, e.g., the position 226, the amplitude is taken to be the signal V(f,x) of the position 226 using the mean value of the signals in the range 226-1∼226-2. This duration, even at its largest, must have a size on the order of that of the pixel. That is, the above-described method takes the mean value of the signals in the pixel bounded by scanning lines i and j. However, if the scanning lines fall within i-j, then the mean value of an interval of a duration smaller than (i-j) is permissible. The distribution of $\bar{\alpha}$ is stored in the memory 10.

We will now discuss an algorithm for obtaining the reflection coefficient R.

As mentioned above, the reflection coefficient R is sequentially obtained from the coefficient R(f,x$_o$) of the reflection from the surface (x=x$_o$) of the object under investigation. The method illustrated in FIG. 25, rather than being a method of obtaining the reflection coefficient of a specific ROI interval, is an algorithm for finding the distribution of the reflection coefficient of a certain scanning line interval.

The foregoing will now be described in detail. x$_m$ is a position corresponding to $x_m = c_0 t_m$, with $x_o = 0$, $t_o = 0$ defining the origin of the surface of the object under investigation. Further, $\bar{\alpha}_{m-1,m}$ is the mean attenuation coefficient of a pixel (i, i+Δi, m−1, m), the coefficient having been obtained through the method of FIG. 15 and stored in the memory 10. Note that $j=i+\Delta i$. In other words, we arrive at the following equation from Eq. (21):

$$\bar{\alpha}_{m-1,m} = \frac{1}{4fC_0(t_m - t_{m-1})} \ln\left[\frac{V(f,x_{m-1})}{V(f,x_m)} \cdot \right. \qquad (22)$$

$$\left. \frac{U(f,x_m)}{U(f,x_{m-1})} \cdot \frac{V(f,L-x_m)}{V(f,L-x_{m-1})} \cdot \frac{U(f,L-x_{m-1})}{U(f,L-x_m)}\right]$$

Therefore, we may write:

$$k_{m-1,m} = \frac{\hat{R}(f,x_{m-1})}{\hat{R}(f,x_m)} = \left[\frac{V(f,x_{m-1})}{U(f,x_{m-1})} \Big/ \frac{V(f,x_m)}{U(f,x_m)}\right] \cdot \qquad (23)$$

$$\exp[-2C_0(t_m - t_{m-1})\bar{\alpha}_{m-1,m}]$$

Figure 25:
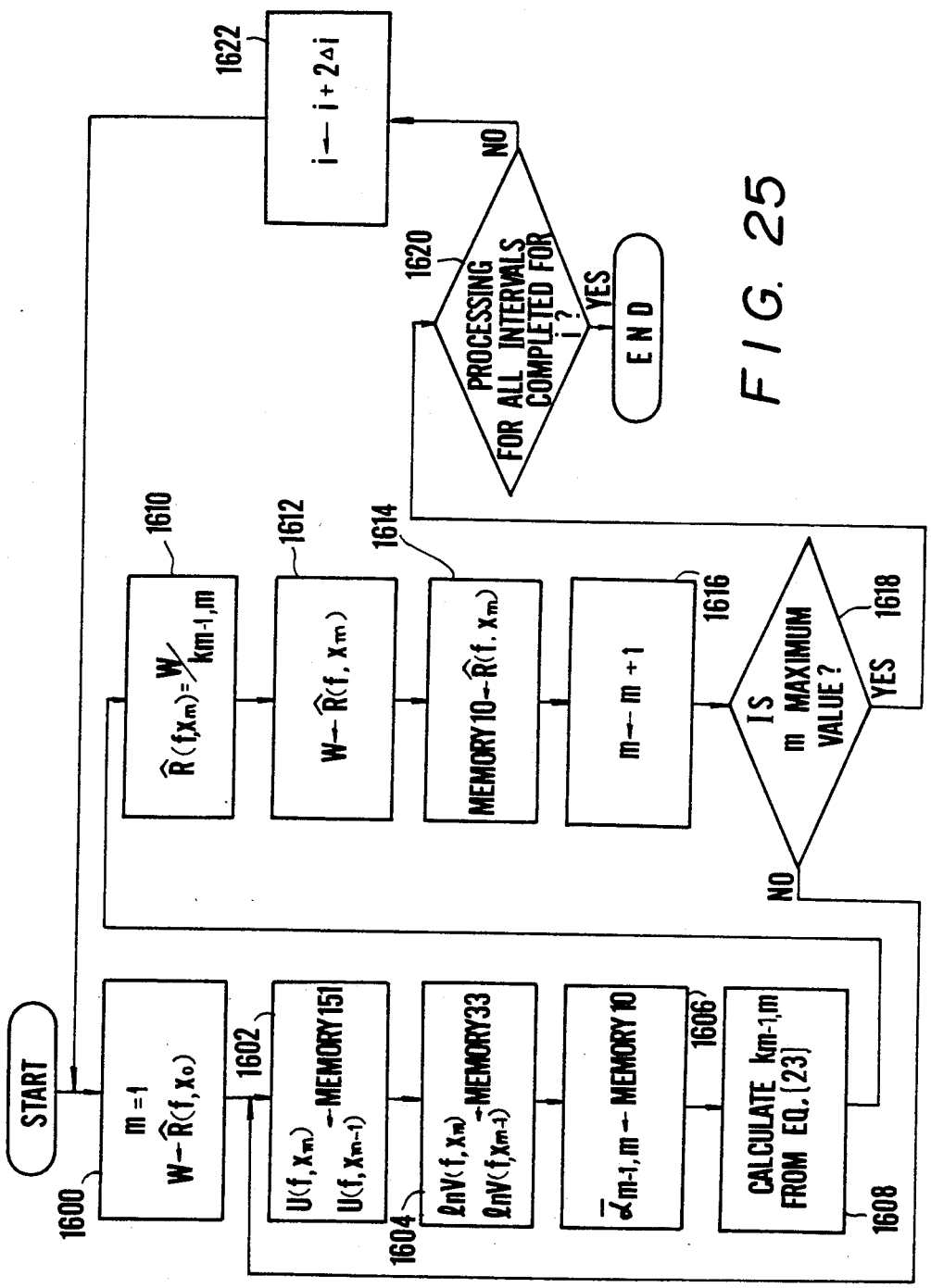
FIG. 25 is a flowchart showing arithmetic operations for displaying acoustic characteristics as a picture of a distribution.

In the flowchart of FIG. 25, the CPU 150 executes a step 1600 to set a counter m within the memory 151 to 1 and store the known value of $\hat{R}(f,x_o)$ in a working register W within the memory 151. Next, in a step 1602, a standard echo intensity U(f,x) is addressed by the value of m to fetch U(f,x$_m$), U(f,x$_{m-1}$). This is followed by execution of a step 1604, in which the memory 33 is addressed by the value of m from the A-mode signals added and averaged in the interval i, i+Δi of the memory 33. The program then moves to a step 1606, in which $\bar{\alpha}_{m-1,m}$ is fetched from the memory 10, and then to a step 1608, in which computing means 32 (FIG. 12(b)) is made to calculate $k_{m-1,m}$ in accordance with Eq. (23). Thus, when m=1 holds, $k_{01}$ is calculated. The next step 1610 calls for the computing means 32 to calculate $\hat{R}(f,x_m) = W/k_{m-1,m}$. When m=1 holds, the status of the register w at step 1600 is $\hat{R}(f,x_o)$, so that $\hat{R}(f,x_1)$ can be calculated. Next, in a step 1612, the status of the register W is replaced with $\hat{R}(f, x_m)$ and, in the following step 1614, $\hat{R}(f,x_m)$ is stored in the memory 10. The value of m is then incremented in a step 1616.

Figure 26:
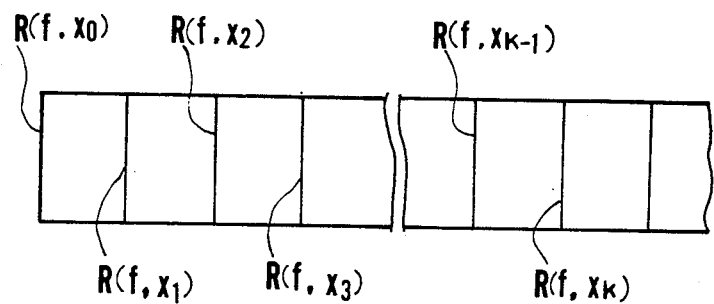
FIG. 26 is a schematic view of an ultrasonic reflection coefficient distribution for describing measurement of ultrasonic reflection coefficient with regard to the flowchart of FIG. 25.

Next, in a step 1618, a decision in rendered as to whether m has attained the maximum value possible. If it has not, processing from step 1602 onward is repeated. The next pixel $\hat{R}(f,x_{m+1})$ is calculated in this manner. The reflection coefficients in the interval of the scanning lines i, i+Δi will be obtained in the manner shown in FIG. 26, which serves as one example.

If all processing for one interval has been completed, a decision is rendered in the next step 1620 as to whether the processing for all intervals has been completed with regard to i. If the decision is negative, the next interval i+Δi~i+2Δi is determined in a step 1622, followed by repeating the process steps from step 1600 onward. Thus, in accordance with the foregoing processing, reflection coefficients over the entire region of the object 15 are obtained.

It should be noted that the flowchart for obtaining reflection coefficient and the flowchart for obtaining the mean attenuation coefficient $\bar{\alpha}$ have been described separately for the sake of convenience. It should be obvious, however, that the two flowcharts may be combined. In other words, it should be appreciated that the reflection coefficient R can be obtained each time the process for finding the mean attenuation coefficient $\bar{\alpha}$ of the pixel (i,i+Δi,m−1,m) is executed. In addition, since the distribution of $\bar{\alpha}$ and R obtained in this manner are stored in the same memory 10, a picture of $\bar{\alpha}$ and of the distribution of R can be obtained by luminance-modulating R in the form of B-mode pictures, and displaying them on the display unit 7 via the picture output amplifier circuit 26.

Figure 27:
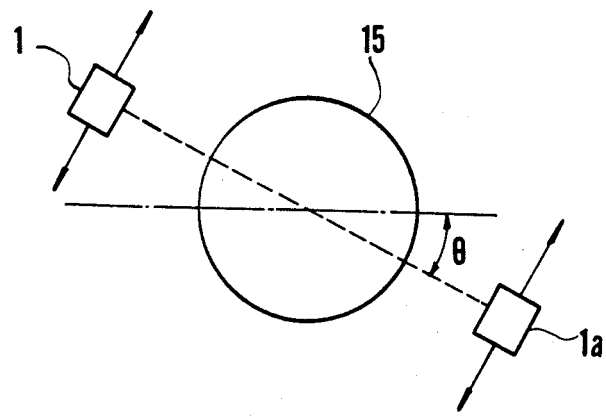
FIGS. 27, 28 and 29 are schematic views useful in describing still another embodiment of the present invention.
Figure 28:
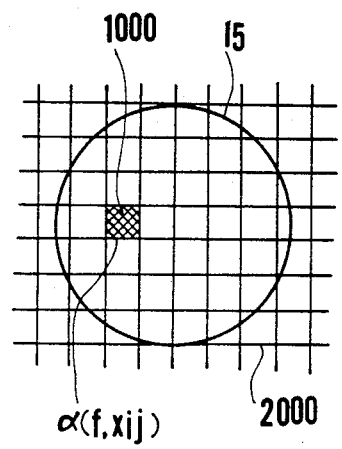
Figure 29:
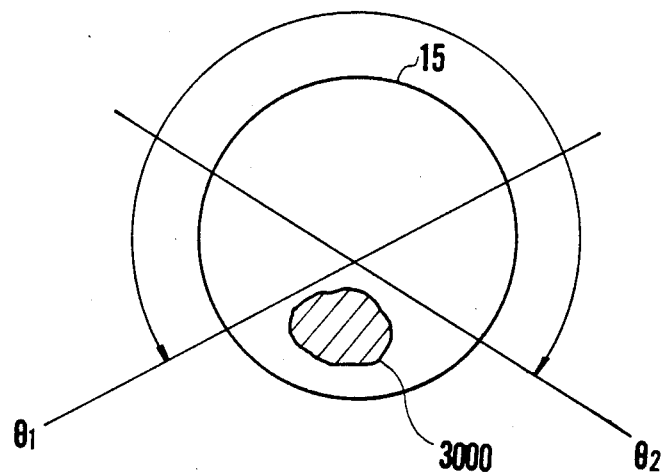

In order to measure the distribution of the attenuation coefficient α(f,x) accurately, the measurements performed by the opposing probes 1, 1a are taken through an angle of 180° along the periphery of the object 15, as shown in FIGS. 27 and 28. The attenuation coefficients $\alpha_\theta(f,x_{ij})$ for respective pixels obtained as the angle changes are added and averaged, with the result being denoted $\alpha(f,x_{ij})$. More specifically, we have the following:

$$\alpha(f,x_{ij}) = \frac{1}{N} \sum_{\theta=0}^{180°} \alpha_\theta(f,x_{ij})$$

where N=180°/Δθ, in which Δθ is the amount by which the angle of observation is incremented with each measurement. Though this method is exactly the same as that used for X-ray CT, a major characterizing feature is that a special image reconstruction algorithm of the kind used in X-ray CT is unnecessary. Finding α(f,x) by measurement over angles ranging from 180° to 0° in this manner results in a reduction, by way of averaging, of errors ascribable to the above-described assumption that R(f,x)≃R(f,L−x) holds when applying the present invention. The present measurement relies upon an algorithm that does not necessarily require measurement data over 180°, as in X-ray CT. Therefore, when there is a portion 3000 within the object 15 through which ultrasonic waves do not penetrate, as shown in FIG. 29, it is possible to exclude this region and perform scanning and measurement from $\theta_1$ to $74_2$.

In the embodiment described above, sweeping by the probes 1, 1a is performed with a single scan. Alternatively, however, scanning may be performed by probe 1 or 1a and the A-mode signals obtained thereby may be stored in the memory 9 to effect a B-mode display. A portion the attenuation coefficient whereof is desired to be measured is set on the B-mode picture through a method similar to that described earlier. If the setting is made as shown in FIG. 14, the controller 8 instructs the scanning mechanism 14 to move the probes 1, 1a to the position of scanning line 200. Here the controller 8 drives the transmitting circuit 23 and controls the switching circuit 13 to perform a scan of several lines about the scanning line 200. This scanning operation is performed independently in alternating fashion from the left and right by the probes 1, 1a. The A-mode signals are again applied to the memory circuit 9, and the mean attenuation coefficient $\bar{\alpha}$ of the ROI interval is measured on the basis of the A-mode signals in accordance with the flowchart of FIGS. 15(a)–15(c).

Figure 17:
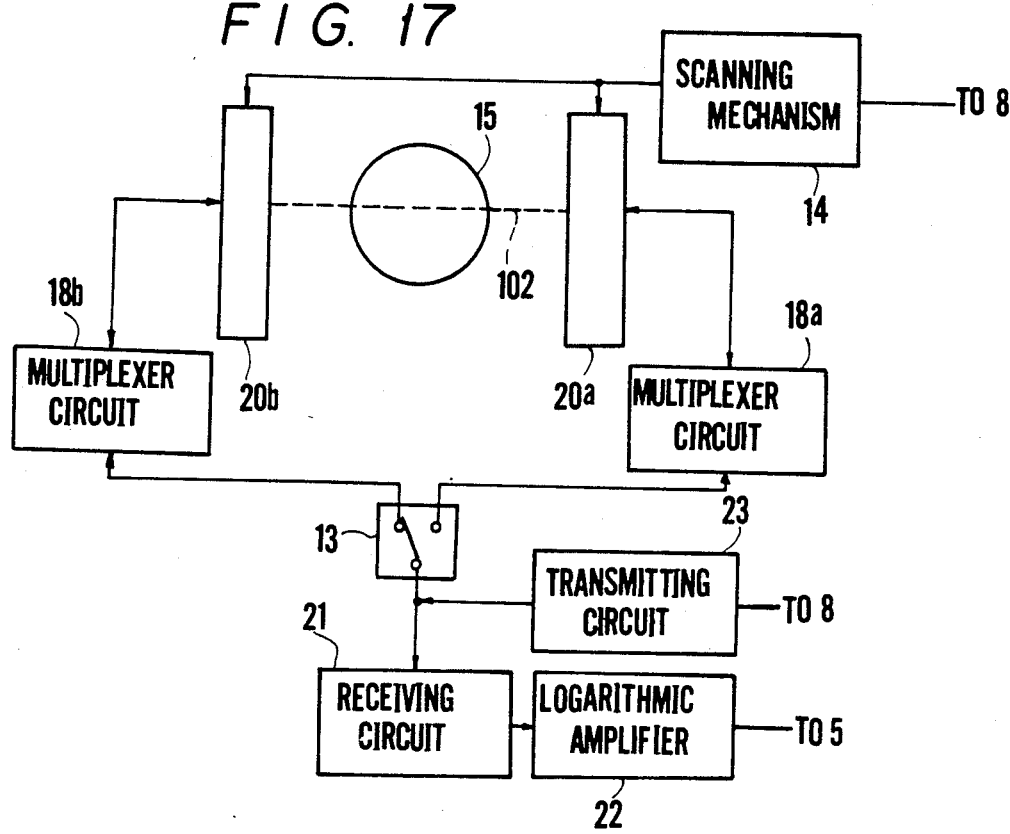
FIGS. 17 and 18 are views showing, in part, another embodiment of the present invention.
Figure 18:
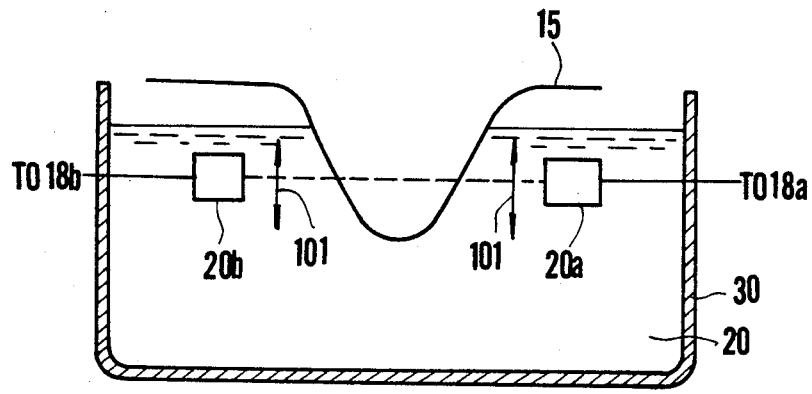

It goes without saying that if linear arrays of probes 20a, 20b are used in place of the probes 1, 1a, as shown in FIGS. 17 and 18, a scan along the scanning direction 100 may be performed electronically to obtain a B-mode picture in real time. Since the electrical circuitry for such an arrangement is the same as that of the conventional linear array scanner, a detailed description thereof need not be given here. The blocks 18a, 18b in FIG. 17 are multiplexer circuits for electronic scanning. Though the receiving circuit 21 includes a phase adjustment circuit for so-called electronic focusing, the circuitry from the logarithmic amplifier circuit 22 onward may be fundamentally the same as that shown in FIG. 12.

Though the foregoing embodiment deals with a breast as the object under investigation, the invention may also be applied to examination of the human abdomen, as will now be described in connection with an embodiment illustrated in FIG. 20.

Figure 1:
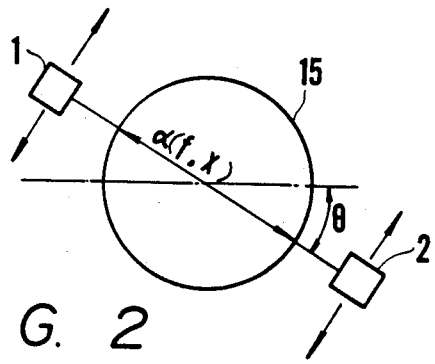
FIGS. 1 and 2 are schematic views useful in describing an example of a method of measuring the acoustic characteristics of an object according to the prior art.
Figure 2:
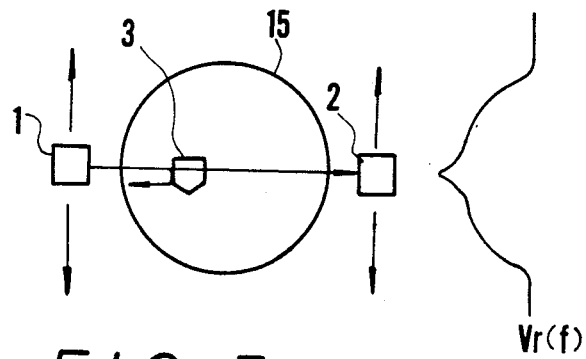
Figure 20:
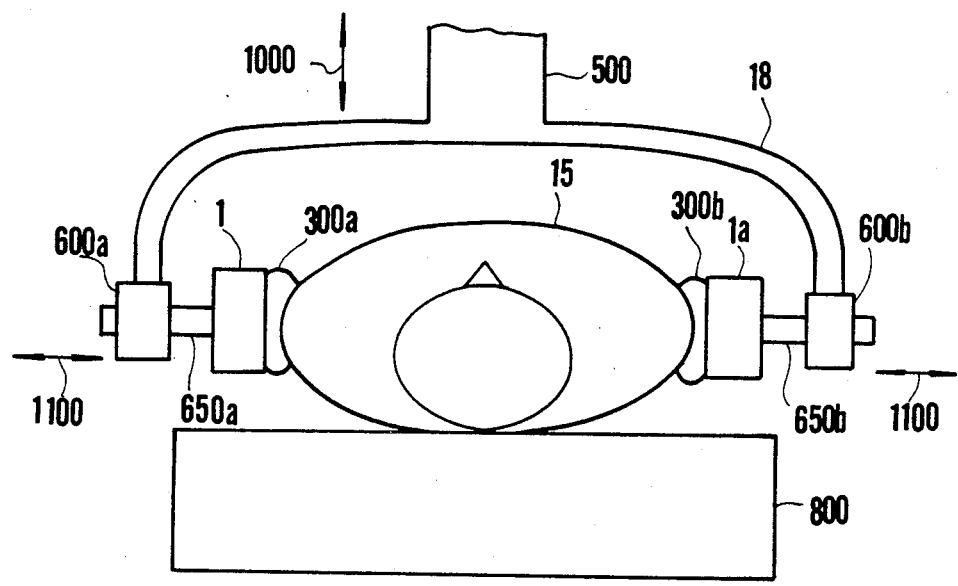
FIGS. 20 and 21 are schematic views useful in describing an example of a method of examining the torso of a human body in accordance with the embodiment of FIG. 12.
Figure 21:
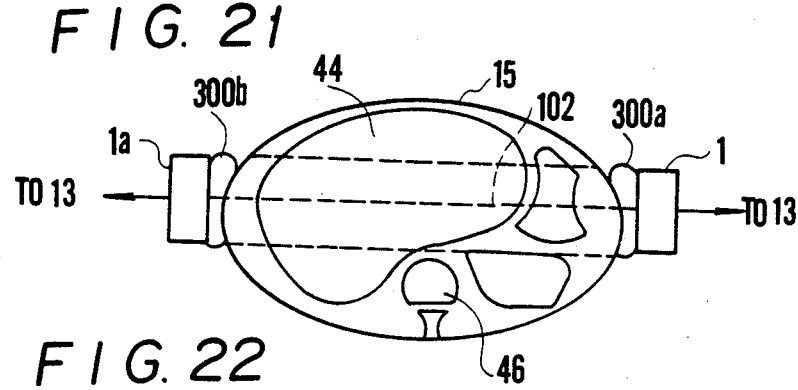

In FIG. 20, a patient which is the object 15 lies prone with his back to a table 800, and the probes 1, 1a are attached to the arm 18 by supports 650a, 650b, 600a, 600b. The arm 18 is held by a support 500. The region to be scanned is set by moving the support 500 along the vertical direction 1000. The probes 1, 1a are provided with water bags 300a, 300b, respectively, for achieving good acoustic contact between the probes and the patient's body. Moving the supports 650a, 650b in the lateral direction 1100 sets the probes 1, 1a to face the patient 15. The measurement cross-section in this case is as shown in FIG. 21, by way of example, with the liver 44 being the object of examination. In such case the spinal column 46 will serve as an obstacle to measurement with the conventional measurement method, e.g., the method described earlier with reference to FIG. 1. In accordance with the method of the present invention, however, measurements are taken from two directions so that the presence of the spinal column 46 is not an impediment. Here the most preferred arrangement is to use electronic scanning-type probes, such as the linear arrays of probes 20a, 20b, in place of the probes 1, 1a.

While the present invention theoretically measures the attenuation coefficient and reflection coefficient of a living body through use of a single frequency, the frequency dependence of the attenuation coefficient can be measured if a similar measurement is performed based on pulse echos having a plurality of different frequencies or a wide frequency band.

According to the present invention as described and illustrated above, the attenuation coefficient and scattering coefficient (reflection coefficient) of an object under investigation can be measured upon being isolated from each other, an achievement not heretofore realized with the prior art. It is also possible to convert the distribution of attenuation coefficients into a picture. The invention also has a number of advantages over the conventional arrangement in which a picture of an attenuation distribution is obtained by a penetration method. Specifically, (a) there is no influence from scattering intensity, (b) a special algorithm for image reconstruction of the kind typified by a filtered back projection is unnecessary, (c) an attenuation distribution picture is obtained in real time, and (d) an attenuation distribution picture can be obtained even with projection data for one direction, thereby widening the field of clinical application in comparison with the transmission method. Another advantage over the prior art is that a measurement can be made using a single frequency, namely pulses of a narrow band. This makes it possible to measure attenuation coefficient (reflection coefficient), attenuation coefficient distribution and reflection coefficient distribution, these not being measurable with the conventional B-mode picture. Obtaining distribution pictures such as these enables qualitative differences in tissue to be ascertained.

As many apparently widely different embodiments of the present invention can be made without departing from the spirit and scope thereof, it is to be understood that the invention is not limited to the specific embodiments thereof except as defined in the appended claims.

What I claim is:

1. An ultrasonic measurement method for measuring acoustic characteristics of an object under investigation by transmitting ultrasonic pulses into the object and detecting an ultrasonic echo signal reflected from within the object, said method comprising:
    a first detection step of transmitting ultrasonic pulses into the object from a first direction and detecting a first ultrasonic echo signal reflected from within the object;
    a second detection step of transmitting ultrasonic pulses into the object from a second direction opposite to the first direction and detecting a second ultrasonic echo signal reflected from within the object;
    an identifying step of identifying first and second echo pulses, corresponding to a region of interest within the object, from the first and the second ultrasonic echo signals, respectively, and
    a computation step of calculating acoustic characteristics of the region of interest from the amplitude values of the first and the second echo pulses identified in said identifying step.

2. The ultrasonic measurement method according to claim 1, wherein the acoustic characteristics include an ultrasonic attenuation coefficient.

3. The ultrasonic measurement method according to claim 2, wherein said computation step includes calculating an attenuation coefficient of the region of interest based on a ratio between the amplitude values of two of said identified first echo pulses for two boundaries in the region of interest where the acoustic characteristics are discontinuous, and a ratio between the amplitude values of two of said identified second echo pulses for said two boundaries.

4. The ultrasonic measurement method according to claim 3, wherein the acoustic characteristics include a reflection coefficient of the ultrasonic waves, and said computation step includes calculating the reflection coefficient from the region of interest based on the calculated attenuation coefficient.

5. The ultrasonic measurement method according to claim 1, wherein said first and second detection steps are performed using a plurality of measurement directions relative to the object under investigation, and said computation step includes calculating the acoustic characteristics using a mean value of results obtained for the plurality of measurement directions.

6. An ultrasonic measurement apparatus for measuring acoustic characteristics of an object under investigation by transmitting ultrasonic pulses into the object and detecting an ultrasonic echo signal reflected from within the object, said apparatus comprising:
    ultrasonic transceiving means for transmitting ultrasonic pulses into the object from a first direction and detecting a first ultrasonic echo signal reflected from within the object, and for transmitting ultrasonic pulses into the object from a second direction opposite to the first direction and detecting a second ultrasonic echo signal reflected from within the object;
    pulse identifying means for identifying first and second echo pulses corresponding to a region of interest within the object, from the first and the second ultrasonic echo signals detected by said ultrasonic transceiving means, respectively;
    arithmetic means for calculating the acoustic characteristics of the region of interest from the amplitude values of the first and the second echo pulses identified by the pulse identifying means; and
    display means for displaying the calculated acoustic characteristics in the form of a visible image corresponding to the region of interest.

7. An ultrasonic measurement apparatus according to claim 6, wherein the acoustic characteristics include an ultrasonic attenuation coefficient.

8. An ultrasonic measurement apparatus according to claim 6, wherein the acoustic characteristics include the reflection coefficient of the ultrasonic waves.

9. An ultrasonic measurement apparatus according to claim 6, wherein said ultrasonic transceiving means includes scanning means for scanning the object under investigation in a direction which is substantially perpendicular to the first direction;
    said arithmetic means includes memory means for storing the first and the second echo signals detected for each scan by the scanning means, said pulse identifying means includes means for identifying two pairs of first and second echo pulses at two boundaries of each of a plurality of sections obtained by subdividing a cross-section of the region of interest formed, by said scanning operation, from the first and the second echo signals stored in said memory means, and
    said arithmetic means includes means for calculating at least one of an ultrasonic attenuation coefficient and a reflection coefficient of each section from the amplitude values of said two pairs of the identified first and second echo pulses; and
    said display means displays at least one of the calculated attenuation coefficient and reflection coefficient of each section in the form of a distribution image thereof in cross-section.

10. An ultrasonic measurement apparatus according to claim 6, wherein said ultrasonic transceiving means scans the object from a plurality of measurement directions relative to the object, and said arithmetic means calculates acoustic characteristics using a mean value of results obtained for the plurality of measurement directions.

* * * * *